US008722668B2

(12) United States Patent
Hochman

(10) Patent No.: US 8,722,668 B2
(45) Date of Patent: May 13, 2014

(54) METHODS AND COMPOSITIONS FOR THE TREATMENT OF NEUROPATHIC PAIN AND NEUROPSYCHIATRIC DISORDERS

(76) Inventor: Daryl W. Hochman, Bahama, NC (US)

( * ) Notice: Subject to any disclaimer, the term of this patent is extended or adjusted under 35 U.S.C. 154(b) by 1781 days.

(21) Appl. No.: 11/101,000

(22) Filed: Apr. 7, 2005

(65) Prior Publication Data

US 2005/0267103 A1    Dec. 1, 2005

Related U.S. Application Data

(63) Continuation-in-part of application No. 10/056,528, filed on Jan. 23, 2002, now Pat. No. 7,214,711, and a continuation-in-part of application No. 09/470,637, filed on Dec. 22, 1999, now Pat. No. 6,495,601.

(60) Provisional application No. 60/263,830, filed on Jan. 23, 2001, provisional application No. 60/113,620, filed on Dec. 23, 1998.

(51) Int. Cl.
*A61K 31/55*    (2006.01)

(52) U.S. Cl.
USPC ........................................ 514/223.2

(58) Field of Classification Search
CPC .. C07D 285/24; C07D 417/04; C07D 285/30; C07D 417/12; A61K 31/54
USPC ........................................ 514/223.2
See application file for complete search history.

(56) References Cited

U.S. PATENT DOCUMENTS

| | | | |
|---|---|---|---|
| 3,634,583 A | 1/1972 | Feit | |
| 3,665,002 A | 5/1972 | Popelak | |
| 3,676,454 A | 7/1972 | Vida | 260/309.5 |
| 3,806,534 A | 4/1974 | Feit | |
| 3,971,819 A | 7/1976 | Feit | |
| 3,985,777 A | 10/1976 | Feit | |
| 3,991,097 A | 11/1976 | Bormann et al. | |
| 4,005,201 A | 1/1977 | Yurugi et al. | |
| 4,010,273 A | 3/1977 | Bormann | |
| 4,018,929 A | 4/1977 | Delarge | |
| 4,154,652 A | 5/1979 | Sawamura | |
| 4,247,550 A | 1/1981 | Feit et al. | |
| 4,261,985 A | 4/1981 | Biollaz | |
| 4,309,348 A | 1/1982 | Asselin et al. | |
| 4,340,737 A | 7/1982 | Johnson | |
| 4,351,833 A | 9/1982 | Johnson | |
| 4,663,348 A | 5/1987 | Chafetz | |
| 4,736,307 A | 4/1988 | Salb | |
| 4,768,513 A | 9/1988 | Suzuki | |
| 4,788,180 A | 11/1988 | Bloch | |
| 4,855,289 A | 8/1989 | Wester et al. | |
| 4,895,807 A | 1/1990 | Cherksey | |
| 4,931,305 A | 6/1990 | Karppanen et al. | |
| 4,972,331 A | 11/1990 | Chance | |
| 4,973,600 A | 11/1990 | Takamura et al. | |
| 5,034,109 A | 7/1991 | Fujibayashi et al. | |
| 5,073,641 A | 12/1991 | Bundgaard et al. | |
| 5,114,957 A | 5/1992 | Hendler et al. | |
| 5,128,327 A | 7/1992 | Chakravarty | |
| 3,058,882 A | 10/1992 | Sturm | |
| 5,162,325 A | 11/1992 | Chakravarty | |
| 5,201,318 A | 4/1993 | Rava | |
| 5,215,095 A | 6/1993 | Macvicar et al. | |
| 5,256,687 A | 10/1993 | Becker | |
| 5,318,024 A | 6/1994 | Kittrell | |
| 5,369,496 A | 11/1994 | Alfano et al. | |
| 5,413,108 A | 5/1995 | Alfano | |
| 5,438,989 A | 8/1995 | Hochman et al. | |
| 5,465,718 A | 11/1995 | Hochman et al. | |
| 5,475,008 A | 12/1995 | Carling et al. | |
| 5,486,530 A | 1/1996 | Boelke et al. | 514/347 |
| 5,498,519 A | 3/1996 | Rubin et al. | 435/1.2 |
| 5,507,287 A | 4/1996 | Palcic et al. | |
| 5,571,842 A | 11/1996 | Kleemann et al. | 514/618 |
| 5,585,401 A | 12/1996 | Brandt et al. | 514/562 |
| 5,627,077 A | 5/1997 | Dyllick-Brenzinger et al. | |
| 5,654,335 A | 8/1997 | Schoenwald et al. | |
| 5,658,786 A | 8/1997 | Smith et al. | 435/365 |
| 5,660,181 A | 8/1997 | Ho et al. | |
| 5,699,798 A | 12/1997 | Hochman et al. | |
| 5,706,821 A | 1/1998 | Matcher et al. | |
| 5,713,352 A | 2/1998 | Essenpreis et al. | |
| 5,753,651 A | 5/1998 | De Padova | |
| 5,763,491 A | 6/1998 | Brandt et al. | |
| 5,807,261 A | 9/1998 | Benaron et al. | |
| 5,834,466 A | 11/1998 | Ramasamy et al. | 514/227.5 |

(Continued)

FOREIGN PATENT DOCUMENTS

| | | |
|---|---|---|
| CA | 2356460 | 6/2000 |
| DE | 2517183 | 4/1975 |

(Continued)

OTHER PUBLICATIONS

E. Eisenberg et al., "Antiepileptic Drugs in the Treatment of Neuropathic Pain", Drugs, 2007, 67(9), pp. 1265-1289.*
M.A. Collins et al., "Brain damage due to episodic alcohol exposure in vivo and in vitro: furosemide neuroprotection implicates edema-based mechanism", FASEB J., 1998, 222, pp. 221-230.*
Palfrey et al, J. Exp. Biol., 1983, 106, 43-54.*
Haas et al, J. Bioenerg & Biomembr., 1998, 30(2), 161-172.*
Isenring et al, J. Biol. Chem., 1998, 273(18), 11295-11301.*
Laird, J. et al., "Presynaptic Inhibition and Spinal Pain Processing in Cition-Chloride Co-Transporter in Hyperalgesia", Neuroscience Letters 20040506 IE, vol. 361, No. 1-3, pp. 200-203.

(Continued)

*Primary Examiner* — Jason Sims
*Assistant Examiner* — Ibrahim D Bori

(57) ABSTRACT

The present invention relates to methods and compositions for treating neuropathic pain and neuropsychiatric disorders by administering agents that are effective in reducing the effective amount, inactivating, and/or inhibiting the activity of a $Na^+$—$K^+$-$2Cl^-$ (NKCC) cotransporter. In certain embodiments, the $Na^+$—$K^+$-$2Cl^-$ co-transporter is NKCC1.

13 Claims, 8 Drawing Sheets

(56) References Cited

U.S. PATENT DOCUMENTS

| | | | |
|---|---|---|---|
| 5,840,035 | A | 11/1998 | Heusmann et al. |
| 5,845,639 | A | 12/1998 | Hochman et al. |
| 5,854,851 | A | 12/1998 | Bamberger et al. |
| 5,855,205 | A | 1/1999 | Papaionnou |
| 5,865,738 | A | 2/1999 | Morcos et al. |
| 5,866,074 | A | 2/1999 | Chapman et al. |
| 5,902,732 | A | 5/1999 | Hochman .................. 435/29 |
| 5,976,825 | A | 11/1999 | Hochman .................. 435/29 |
| 6,040,331 | A | 3/2000 | Yamamoto et al. |
| 6,130,234 | A | 10/2000 | Bigge et al. |
| 6,228,873 | B1 | 5/2001 | Brandt et al. |
| 6,369,094 | B1 | 4/2002 | Bentley et al. |
| 6,395,781 | B1 | 5/2002 | Roman et al. |
| 6,420,405 | B2 | 7/2002 | Inada et al. |
| 6,432,986 | B2 | 8/2002 | Levin |
| 6,495,601 | B1 * | 12/2002 | Hochman .................. 514/562 |
| 6,608,047 | B2 | 8/2003 | MacLaughlan et al. |
| 6,669,951 | B2 | 12/2003 | Rothbard et al. |
| 6,834,238 | B1 | 12/2004 | Hochman |
| 6,894,030 | B2 | 5/2005 | Hartley |
| 7,199,139 | B2 | 4/2007 | Takaoka et al. |
| 7,214,711 | B2 | 5/2007 | Hochman |
| 7,282,519 | B2 | 10/2007 | Garvey et al. |
| 2002/0082252 | A1 * | 6/2002 | Hochman .................. 514/217 |
| 2002/0147197 | A1 | 10/2002 | Newman et al. |
| 2005/0065086 | A1 | 3/2005 | Kirk et al. |
| 2005/0203169 | A1 | 9/2005 | Moskowitz |
| 2005/0234107 | A1 | 10/2005 | Wank |
| 2005/0267103 | A1 | 12/2005 | Hochman |
| 2006/0025387 | A1 | 2/2006 | Hochman |
| 2006/0035914 | A1 | 2/2006 | Hochman |
| 2006/0089350 | A1 | 4/2006 | Hochman |
| 2006/0111397 | A1 | 5/2006 | Moskowitz |
| 2007/0043034 | A1 | 2/2007 | Staley et al. |
| 2007/0085269 | A1 | 4/2007 | Martin et al. |
| 2007/0092510 | A1 | 4/2007 | De Koninck et al. |
| 2007/0149526 | A1 | 6/2007 | Hochman et al. |
| 2007/0155729 | A1 | 7/2007 | Morgan et al. |
| 2007/0293463 | A1 | 12/2007 | Dittrich et al. |
| 2009/0215754 | A1 | 8/2009 | Hochman |
| 2009/0258844 | A1 | 10/2009 | Hochman |

FOREIGN PATENT DOCUMENTS

| | | |
|---|---|---|
| GB | 2207129 | 1/1999 |
| JP | 49/81334 | 6/1974 |
| JP | 06-040902 | 2/1994 |
| JP | 10-509178 | 9/1998 |
| JP | 10-512851 | 12/1998 |
| WO | WO 00/37616 | 6/2000 |
| WO | WO 03/013434 | 2/2003 |
| WO | WO 2005/039637 | 5/2005 |
| WO | WO 2005/082350 | 9/2005 |
| WO | WO 2006/024913 | 3/2006 |
| WO | WO 2006/058008 | 6/2006 |
| WO | WO 2006/089350 | 8/2006 |
| WO | WO 2006/110187 | 10/2006 |
| WO | WO 2007/042504 | 4/2007 |
| WO | WO 2007/047447 | 4/2007 |
| WO | WO 2007/047698 | 4/2007 |
| WO | WO 2008/052190 | 5/2008 |
| WO | WO 2010/085352 | 7/2010 |

OTHER PUBLICATIONS

Sung, K W et al: "Abnormal GABAA receptor-mediated currents in dorsal root ganglion neurons isolated from Na-K-2Cl cotransporter null mice." The Journal of Neuroscience : The Official Journal of the Society for Neuroscience Oct. 15, 2000, vol. 20, No. 20, Oct. 15, 2000, pp. 7531-7538, XP002523056.

Database Biosis [Online] Biosciences Information Service, Philadelphia, PA, US; 2003, Valencia De Ita S et al: "The Role of the Na+—K+-2Cl—Cotransporter in the Development of Capsaicin-Induced Neurogenic Inflammation." XP002523057.

Delpire, E. et al., "Human and Murine Phenotypes Associated with Defects in Cation-Chloride Cotransport", Annual Review of Physiology 2002 US, vol. 64, pp. 803-843, XP002523054.

Granados-Soto, V. et al., "Peripheral and Central Antinociceptive Action of N<+>—K<+>—2Cl<–> Cotransporter Blockers on Formalin-Induced Nociception in Rats", Pain Elsevier Science publishers, Amsterdam, NL, vol. 114, No. 1-2, Mar. 2005.

Haglund, M. et al., "Furosemide and Mannitol Supperssion of Epileptic Activity in the Human Brain", Journal of NeuroPhysiology 200508 US, vol. 94, No. 2, XP002523053, pp. 907-918, Aug. 2005.

Laird, J. et al., "Presynaptic Inhibition and Spinal Pain Processing in Cition-Chloride Co-Transporter in Hyperalgesia", Neuroscience Letters 20040506 IE, vol. 361, No. 1-3 pp. 200-203, May 6, 2004.

Sung, K W et al: "Abnormal GABAA receptor-mediated currents in dorsal root ganglion neurons isolated from Na—K-2C1 cotransporter null mice." The Journal of Neuroscience : The Official Journal of the Society for Neuroscience Oct. 15, 2000, vol. 20, No. 20, pp. 7531-7538, XP002523056.

Extended European Search Report for International Application No. PCT/US2005/043177, mailed Jun. 4, 2009.

Dorwald, F.A., Side Reactions in Organic Synthesis, 2005, Wiley, VCH, Weinheim, p. IX of Preface.

Luddens, et al. "Structure—activity relationship of furosemide-derived compounds as antagonists of cerebellum-specific $GABA_A$ receptors." European J. of Pharmacology (Mar. 5, 1988) 344(2-3): 269-277.

Ngohou-Bonevat, et al., "Treatment of Convulsive Eclampsia Crisis by Therapeutic Combination; Diazepam Dihydralazine, Furosemide" Bulletin de la Federation des Societes de Gynecologie et d'Obstetrique de Langue Française (1971).

"The Migraineur's Guide to Migraine" http://www.headachecare.com (2000).

Abrams Journal of Clinical Pharmacology (1981) 21:673-679.

Ahmad, et al. "Controlled Trial of Furosemide as an Antiepileptic Drug in Focal Epilepsy" J Clin Pharmacol (1976) 3:621-625.

Akerman, et al. "Topiramate inhibits cortical spreading depression in rat and cat: impact in migraine aura" Neuroreport (2005) 16(12):1383-7 [Abstract].

Barbaro, et al. "A Potential Role for Astrocytes in Mediating the Antiepileptic Actions of Furosemide In Vitro" Neuroscience (2004) 128:655-663.

Alberts, et al. (1994) "Molecular Biology of the Cell" $3^{rd}$ Edition, pp. 951-953.

A. Barth, L. B. Nguyen, L. Barth, J. T. Ho, D. W. Hochman, D. W. Newell, "Optical imaging of acute ischemic injury in hippocampal slice cultures." Poster presentation at 1996 Society for Neuroscience meeting.

Batham, et al. "Diazepam in Combination with Antiepileptic Drugs—An Experimental Study" Indian J. Med. Rca. (1977) 66:872-875.

Bazil, et al. "Advances in the Medical Treatment of Epilepsy" Annu. Rev. Med. (1998) 49:135-162.

Baumann and Ulshöfer (1968) "Chemistry and Physics of Lipids" 2(1):114-128 [Abstract].

Bikson, et al. Inhibition of Nonsynaptic Epileptiform Activity in the Hippocampus Society for Neuroscience (1998) 24:1213 [Abstract].

Bundgaard, "Photodegradation and Hydrolysis of Furosemide and Furosemide Esters in Aqueous Solutions" International Journal of Pharmaceutics (1988) 42:217-224.

Bundgaard, et al. "Glycolamide Esters as a Novel Biolabile Producing Type for Non-Steroidal Anti-Inflammatory Caiboxylic Acid Drugs" International Journal of Pharmaceutics (1988) 43:101-110.

Carter, "Status Epilepticus Treated by Intravenous Urea" Epilepsia (1962) 3:198-200.

Collins, et al. "Brain damage due to episodic alcohol exposure in vivo and in vitro: furosemide neuroprotection implicates edema-based mechanism" J. FASEB Journal (1998) 12(2):221-230.

Cragoe, et al. "Agents for the treatment of brain injury. 1. (Aryloxy)alkanoic acids" J. Med. Chem. (May 1982) 25(5):567-579.

Delpire, et al. "Human and Murine Phenotypes Associated with Defects in Cation-Chloride Cotransport" Annual Review of Physiology (2002) 64:803-843.

(56) References Cited

OTHER PUBLICATIONS

Diener, et al. "Emerging Treatments in Headache" European Neurology (1997) 38(3):167-174 [Abstract].
Dzhala, et al. "NKCC1 Transporter Facilitates Seizures in the Developing Brain" Nature Medicine (2005) 11(11):1205-1213.
Echevarria, et al. "Optical Measurement of Osmotic Water Transport in Cultured Cells" J. Gen. Physiol. (Apr. 1992) 99:573-589.
Ebersberger, et al. "Is There a Correlation Between Spreading Depression, Neurogenic Inflammation, and Nociception That Might Cause Migraine Headache?" Ann. Neurol. (Jan. 2001) 49(1):7-13.
Eisenberg, et al. "Antiseptic Drugs in the Treatment of Neuropathic Pain" Drugs (2007) 67(9):1265-1269.
Ellory, et al. "The Human Erythrocyte Cl-Dependent Na-K Cotransport System as a Possible Model for Studying the Action of Loop Diuretics" British Journal of Pharmacology (1982) 75(1):183-188.
Espinosa, "Efecto Anticonvulsivante Del Seguril, Tomo" Med. Esp. (1969) 61(361):280-292.
Ettmayer, et al. "Lessons Learned from Marketed and Investigational Prodrugs" J. Med. Chem. (2004) 47(10): 2394-2404.
Feit, et al. "Purification of Proteins of the Na-Cl Cotransporter from Membranes of Ehrlich Ascites Cells Using a Bumetanide-Sepharose Affinity Column" J. Membrane Bio. (1988) 103:135-147.
Feit, "Aminobenzoic Acid Diuretics. 2.4-Substituted-3-amino-5-sulfamylbenzoic Acid Derivatives" Journal of Med. Chem. (1971) 14(5):432-439.
Ferrary, et al. "CAS Accession # 1993353415" The Journal of Physiology (1993) 461:451-465.
Gamba, et al. "Primary structure and functional expression of a cDNA encoding the thiazide-sensitive, electroneutral sodium-chloride cotransporter" PNAS USA (Apr. 1993) 90:2749-2753.
Gonzalez, et al. "Acetoxymethyl 4-chloro-N-furfuryl-5-sulfamoylanthranilate, an Absorption Furosemide Prodrug Acta Crystallographica" (1996) Section C C52(11): 2875-2878, Chem. Abstracts 126: 25037.
Go and Branen (1975) Journal of American Oil Chemists' Society 52(10): 427-429 [Abstract].
Granados-Soto, et al. "Peripheral and Central Antinociceptive Action of $Na^+$—$K^+$—$2Cl^-$ Cotransporter Blockers on Formalin-Induced Nociception in Rats" Pain (2005) 114:231-238.
Gutschmidt, et al. "Anticonvulsant Actions of Furosemide In Vitro" Neuroscience (1999) 91(4):1471-1481.
Haglund, et al. "Enhanced Optical Imaging of Human Gliomas and Tumor Margins" Neurosurgery (Feb. 1996) 38(2):308-317.
Haglund, et al. "Enhanced Optical Imaging of Rat Gliomas and Tumor Margins" Neurosurgery (Nov. 1994) 35(5): 930-941.
Haglund, et al. "Optical Imaging of Epileptiform and Functional Activity in Human Cerebral Cortex" Nature (1992) 358:668-871.
Haglund and Hochman "Furosemide and Mannitol Suppression of Epileptic Activity in the Human Brain" J. Neurophysiol. (2005) 94:907-918.
Hannaert, et al. "Rat NKCCVNKCCI Cotransporter Selectivity for Loop Diuretic Drugs" Naunyn-Schmiedeberg's Arch. Pharmacol. (2002) 365:193-199.
Hesdorfer, et al. "Are Certain Diuretics Also Anticonvulsants?" Ann. Neurol. (Oct. 2001) 50(4): 458-462.
Hesdorfer, et al. "Severe, Uncontrolled Hypertension and Adult-Onset Seizures: A Case-Control Study in Rochester, Minnesota" Epilepsia (1996) 37(8): 736-741.
Hochman, "Intrinsic Optical Changes in Neuronal Tissue" Neurosurgery Clinics of North America (Jul. 1997) 8(3):393-412.
Hochman, et al. "Extracellular Chloride and the Maintenance of Spontaneous Epileptiform Activity in Rat Hippocampal Slices" Society for Neuroscience (1999) 81:49-59.
Hochman, et al. "Dissociation of Synchronization and Excitability in Furosemide Blockade of Epileptiform Activity" Science (Oct. 6, 1995) 270:99-102.
Hochman, et al. "Chloride-Contransport Blockade Desynchronizes Neuronal Discharge in the Epileptic Hippocampal Slice" J. Neurophysiol. (2000) 83:406-417.
Hochman, et al. "Extracellular Chloride and the Maintenance of Epileptiform Activity in Hippocampal Slices" Society for Neuroscience (1997) 23(2):2425.
Inoue, et al. "Intracerebroventricular injections of ethacrynic acid induced status epilepticus" Eur. J. Pharmacol. (1989) 166(1):101-106.
James, et al. "Cortical spreading depression and migraine: new insights from imaging?" Trends Neurosci. (May 2001) 24(5):266-271 [Abstract].
Jauch, et al. "Effects of Barium, Furosemide, Ouabain and 4,4'-Diisothiocyanatostitbene –2,2'-disulfonic acid (DIDS) on Ionophoretically-Induced Changes in Extracellular Potassium Concentration in Hippocampal Slices from Rats and from Patients with Epilepsy" Brain Research (2002) 925:18-27.
Jeffreys, "Mechanisms and Experimental Models of Seizure Generation" Current Opinion in Neurology (1998) 11:123-127.
Jin, et al. "Impaired Cl extrusion in Layer V Pyramidal Neurons of Chronically Injured Epileptogenic Neocortex" J. Neurophysiol (2005) 93:2117-2126.
Johnson, et al. "Oral Topiramate for Treatment of Alcohol Dependence: A randomised Controlled Trial" Lancet (2003) 361:1677-1685.
Katz, et al. American Heart Journal (1995) 129:359-368.
Kempski, et al. "Glial ion transport and volume control" Ann. N.Y. Mad. Sci. (1991) 633:306-317 [Abstract].
Kimelberg, "Anisotonic media and glutamate-induced ion transport and volume responses in primary astrocyte cultures" J. Physiol. (Paris) (1987) 82(4):294-303 [Abstract].
Kimelberg, et al. "Furosemide- and bumetanide-sensitive ion transport and volume control in primary astrocyte cultures from rat brain" Brain Res. (Dec. 1985) 361(1-2):125-134 [Abstract].
Laird, et al. "Presynaptic Inhibition and Spinal Pain Processing in Cation-Chloride Co-Transporter in Hyperalgesia" Neuroscience Letters (May 6, 2004) 361(1-3):200-203.
Lambert, et al. "Cortical spreading depression reduces dural blood flow a possible mechanism for migraine pain" Cephalalgia (1994) 14(6): 430-436.
Lowenstein, et al. "Status Epilepticus" The New England Journal of Medicine (Apr. 2, 1998) 338(14):970-976.
MacDonald, et al. "Mechanisms of Action of New Antiepileptic Drugs" Current Opinion in Neurology (1997) 10: 121-128.
Langworthy, et al. (1974) J. Bacteriol. 119(1): 106-116 [Abstract].
Margineanu, et al. "Differential Effects of Cation-Chloride Co-Transport-Blocking Diuretics in a Rat Hippocampal Slice Model of Epilepsy" Epilepsy Research (2006) 69:93-99.
Masereel, et al. "Anticonvulsant Activity of Pyrid-3-yl-Sulfonyl Ureas and Thioreas" Epilepsia (1997) 36(3):334-337.
Mathew, et al. "Coexistence of migraine and idiopathic intracranial hypertension without papilledema" Neurology (May 1996) 46(5): 1226-1230.
McElroy, et al. "Topiramate in the Treatment of Binge Eating Disorder Associated with Obesity: A Randomized, Placebo-Controlled Trial" Am. J. Psychiatry (Feb. 2003) 160(2): 255-261.
Mcleod, "The Mysterious Etiology of Head Pain" Medical Sciences Bulletin (1996).
Merkel, et al. "Piretanide (HOE 118) A new high ceiling salidiuretic" European J. of Medicinal Chemistry (Sep.-Oct. 1976) 11(5):399-406.
Merkel, et al. [Selektive Reduktion von Imiden mit funktionellen Gruppen] Liegbigs Ann. Chem. (1979) 4:461-469.
Misiuk, et al. "[Effect of glycerol, mannitol, and lasix on cerebrospinal fluid pressure in the acute period of a stroke,"] [Zhumal Nevropatologii I Psikhiatth Irneni] S. S. Korsakova (1981) 81(8):1149-1152.
Misiuk, et al. "Effect of glycerol, mannitol and lasix on cerebrospinal fluid pressure in the acute period of a stroke" Medline (1981) Abstract.
Mombru, et al. "Two Absorption Furosemide Prodrugs" Acta Crystallographics (1999) Section C C55(3):413-416; Chem. Abstracts 130: 289414.
Mørk, et al. "Furosemide prodrugs: synthesis, enzymatic hydrolysis and solubility of various furosemide esters" International Journal of Pharmaceutics (Apr. 30, 1990) 60(2):163-169.

(56) References Cited

OTHER PUBLICATIONS

Muraki, et al. "Aminoaluminum Hydride as New Reducing Agents. I. Selective Reduction of Carboxylic Acids to Aldehydes" Chem. Letters (1974) 1447-1450 and (1975) Chem. Letters 215-218.

Newell, et al. "Glutamate and Non-Glutamate Receptor Mediated Toxicity Caused by Oxygen and Glucose Deprivation in Organotypic Hippocampal Cultures" The Journal of Neuroscience (Nov. 1995) 15(11):7702-7711.

Ngohou-Bonevat, et al. "Treatment of Convulsive Eclampsia Crisis by Therapeutic Combination; Diazepam, Dihydralazine, Furosemide" [Bulletin Ce La Federation Des Sociates Ce Gynecologie eta C Obsterthque Ce Lan gue Francaise] (Nov.-Dec. 1971). 23(5): 570-571.

Niki, et al. "Effects of JTE-522, a specific inhibitor of cyclooxygenase-2, on the recurrence of allergic inflammation in rats" European J. of Pharmacology (Mar. 5, 1998) 344(2-3):269-277.

Noble, et al. Cm. Synth. CoL (1963) 4:924-927, New York: John Wiley & Sons, Inc.

Obrenovitch, et al. "Inhibition of cortical spreading depression by L-701, 324, a novel antagonist at the glycine site of the N-methyl-D-aspartate receptor complex" British J. of Pharmacology (Mar. 1997) 117(5):931-937.

Parsons, "Cortical Spreading Depression: its Role in Migraine Pathogenesis and Possible Therapeutic Intervention Strategies" Current Pain and Headache Reports (2004) 8:410-416.

Parsons "Recent advances in mechanisms of spreading depression" Current Opinion in Neurology (1998) 11:227-231.

Pasantes-Morales, et al. "Volume-sensitive release of taurine from cultured astrocytes: properties and mechanism" Glia (1990) 3(5):427-32 [Abstract].

Petzinger, et al. "Interaction of bumetanide derivatives with hepatocellular bile acid uptake" Am. J. Physiol. (1993) 265(5):6942-6954.

Pinegin, et al. "Effect of furosemide on intracranial pressure in patients with intracranial hypertension" Medline (1983) [Abstract].

Pinegin, et al. "[Effect of furosemide on intracranial pressure in patients with intracranial hypertension,]" Zhurnal Nevropato-ogii—Psikhiatrii Imeni S. S. Korsakova (1983) 83(5):675-677.

Prandi, et al. "A Bioavailability Study of Furosemide Prodrug in Humans" Acta Farmaceutica Bonaerense (1993) 12(3):131-136; (1995) Chem. Abstracts 122 89212.

Prandi, et al. Studies on the Relation Between Structure-Lipophilicity-Hydrolysis Kinetics of a Combination of Albumin with a Series of Furosemide Prodrugs, [Revista Portuguesa de Farmacia] (1994) 44(4):164-169; 1995 Chem. Abstracts 123:47371.

Prandi, et al. "Development of Absorption Furosemide Prodrugs: Synthesis, In-Vitro and In Vivo Evaluation" II Farmaco (1992) 42(2):249-263.

Prandi, et al. "Bioavailability Study of Furosemide Prodrugs in Rats" II Farmaco (1992) 47(9):1225-1230.

Queste, et al. (2006) Green Chem. 8: 822-830 [Abstract].

Read, et al. "Furosemide inhibits regenerative cortical spreading depression in anaesthetized cats." Cephalagia (Dec. 1997) 17(8): 826-832.

Reed, et al. "The Effect of Hypertonic Urea Solution on Electroshock Seizure Threshold and Electrolyte Distribution in Rats" Reed and Woodbury (1964) 146:154-159.

Reid, et al. "Agents which Block Potassium-Chloride Contransport Prevent Sound-Triggered Seizures in Post-Ischemic Audiogenic Seizure-Prone Rats" Brain Reseamli (2000) 864:134-137.

Rivera, et al. "The W—Cr Co-Transporter KCC2 Renders GABA Hyperpolarizing During Neuronal Maturation" Nature (1999) 397(6716):251-255 [Abstract].

Rozen "Treatment of a Prolonged Migrainous Aura with Intravenous Furosemide" Neurology (Sep. 2000) 55:732-733.

Sato, et al. "Effect of Acetazolamide on the Anticonvulsant Potency of Phenobarbital in Mice" J. Pharm. Dyn. (1961) 4:952-960.

Schlatter, et al. "Effect of 'High Ceiling' Diuretics on Active Salt Transport in the Cortical Thick Ascending Limb of Henle's Loop of Rabbit Kidney: Correlation of Chemical Structure and Inhibitory Potency" Pflügers Arch. (1983) 396:210-217.

Schwartzkroin, et al. "Osmolarity Ionic Flux, and Changes in Brain Excitability" Epilepsy Research (1998) 32:275-285.

Shani, et al. "Structure Activity Correlation for Diuretic Furosemide Congeners" Pharmacology (Mar. 1983) 26(3):172-180.

Shirai, et al. "Acetazolamide Testing of Cerebral Vasodilator Capacity Provokes Vascular But Not Tension Headaches" The Journal of Head and Face Pain (1996) 36(10):589 [Abstract].

Sinha, et al. "Effects of Furosemide on Normal and Epileptiform Evoked Activity in Area CAI of Guinea Pig Hippocampal Slice" Society for Neuroscience (1997) 23(1-2):2425.

Snow, et al. "Electrophysiological and Optical Changes in Slices of Rat Hippocampus During Spreading Depression" J. of Neurophysiology (1983) 50(3):561-572.

Stringer, et al. "Effect of Seizures and Diuretics on the Osmolality of the Cerebrospinal Fluid" Brain Research (1997) 745:328-330.

Sturm, et al. Synthesen von 5-Sulfamoyl-anthranilsaure-Derivaten, Chem. Ber., Weinheim (1966) 99: 326-344.

Suescun, et al. "Three Isostructural Furosemide Prodrugs" Acta Crystallographica (1999) Section C C54(12): 1911-1915; Chem. Abstracts 130: 117642.

Sung, et al. "Abnormal $GABA_A$ receptor-mediated currents in dorsal root ganglion neurons isolated from $Na^+$—$K^+$—$2Cl^-$ cotransporter null mice" The Journal of Neuroscience (Oct. 15, 2000) 20(20): 7531-7538.

Thevis, et al. "Effect of the Location of Hydrogen Abstraction on the Fragmentation of Diuretics in Negative Electrospray Ionization Mass Spectrometry" J. Am. Soc. for Mass Spectrom. (2003) 14:658-610.

Tongia, "Potentiated Anticonvulsant Effect Against Audiogenic Seizure with Furosemide and Diphenylhydantoin Sodium, lnd." J. Physio. Pharmac.—Letter to the Editor (1981) 25(3): 292-294.

Tongia, "Furosemide Suppressing Audiogenic Seizure, md." J. Physiol. Pharmac.—Letter to the Editor (1981) p. 91-92.

Burinex® K, intekom.com, Malahyde Information Systems (1996-2004).

Upton, Mechanisms of Action of New Antiepileptic Drugs: Rational Design and Serendipitous Findings, TiPS (1994) 15:456-463.

Valencia De Ita, et al. (2006) "The Role of the $Na^+$—$K^+$—$2Cl^{31}$ Cotransporter in the Development of Capsaicin—Induced Neurogenic Inflammation." J Neurophysiol 95: 3553-3561.

Verkman "Optical Methods to Measure Membrane Transport Processes" J. of Membrane Biology (1995) 148: 99-110.

Walz "Role of Na—K—Cl cotransport in astrocytes" Can. J. Physiol. Pharmacol. (1992) 70 (Suppt): S260-S262 [Abstract].

Walz "Role of astrocytes in the spreading depression signal between ischemic core and penumbra" Neurosci. Biobehav. Rev. (1997) 21 2. 135-142.

Walz, et al. "Intense Furosemide-Sensitive Potassium Accumulation in Astrocytes in the Presence of Pathologically High Extracellular Potassium Levels" J. Cerebral Blood Flow and Metabolism (1984) 4:301-304.

Welch "Pathogenesis of Migraine" Seminars in Neurology (1997) 17(4):335-341.

Welch Current Opinions in Headache Pathogenesis: Introduction and Synthesis, Current Opinion in Neurology (1998) 11:193-197.

Welch "Cortical Hyperexcitability Seen as Mechanism for Migraine With Aura" Reuters Health Information Bulletin (Jun. 20, 1997).

Welch "Brain Imaging Studies Support Neuroelectric Etiology of Migraine Aura." Reuters Health Information (May 10, 1999).

Welch, et al. "The Concept of Migraine as a State of Central Neuronal Hyperexcitability." Neural Clin (1990) 8: 817-826 [Abstract].

Worthley, et al. "Treatment of Hyponatremic Seizures with Intravenous 29.2% Saline" Br. Med. J. (Jan. 1986) 292: 168-170.

"Strategies for Optimizing Migraine Management" Proceedings From a CME Teleconference Series (Sep. 10-14, 2001) 1-26.

SciFinder search on Furosemide (2006) pp. 1-96.

Niki, et al. European Journal of Pharmacology (1998) 344: 261-267.

Malmberg and Bannon Current Protocols in Neuroscience (1999) 8.9.1-8.9.15.

Le Bars, et al. "Animal Models of Nociception" Pharmacological Reviews (2001) 53(4): 597-652.

(56) References Cited

OTHER PUBLICATIONS

Price, et al. "Chloride regulation in the pain pathway." Brain Research (2009) 1-22.
Pitcher, et al. "Spinal NKCC1 blockade inhibits TRPV1-dependent referred allodynia" Molecular Pain (2007) 3(17): 1-8.
Russell, "Sodium—Potassium—Chloride Cotransport," Physiological Reviews, vol. 80, No. 1, Jan. 2000.
Puschett, Pharmacological Classification and Renal Actions of Diuretics, Cardiology, vol. 84 (1994).
Whiteley and Dalrymple, Current Protocols in Pharmacology (1998) 5.4.1-5.4.3.
Rozen, Todd D., MD, "Treatment of a prolonged migrainous aura with intravenous furosemide," *Neurology*, vol. 55, pp. 732-733 (Sep. 2000).
Collins, Michael A., et al., "Brain damage due to episodic alcohol exposure in vivo and in vitro: furosemide neuroprotection implicates edema-based mechanism," *The FASEB Journal*, vol. 12, pp. 221-230 (Feb. 1998).
Hochman, Daryl W., et al., "Dissociation of Synchronization and Excitability of Furosemide Blockade of Epileptiform Activity," *Science*, vol. 270, pp. 99-102 (Oct. 6, 1995).
Pinegin, L.E., et al., "Effect of furosemide on intracranial pressure in patients with intracranial hypertension," *Abstract—Medline* (1983).
Misiuk, N.S., et al., "Effect of glycerol, mannitol and lasix on cerebrospinal fluid pressure in the acute period of a stroke," *Abstract—Medline* (1981).
Parsons, Andrew W., "Recent advances in mechanisms of spreading depression," *Current Opinion in Neurology*, vol. 11, pp. 227-231 (1998).
Snow, Robert W., et al., "Electrophysiological and Optical Changes in Slices of Rat Hippocampus During Spreading Depression," *Journal of Neurophysiology*, vol. 50, No. 3, pp. 561-572 (Sep. 1983).
Walz, Wolfgang et al., "Intense Furosemide-Sensitive Potassium Accumulation in Astrocytes in the Presence of Pathologically High Extracellular Potassium Levels," *Journal of Cerebral Blood Flow and Metabolism*, vol. 4, pp. 301-304 (1984).
Kimelberg, H.K. et al., "Furosemide- and bumetanide-sensitive ion transport and volume control in primary astrocyte cultures from rat brain," *Abstract—Brain Res.*, vol. 361, Nos. 1-2, pp. 125-134 (Dec. 30, 1985).
Kimelberg, H.K., "Anisotonic media and glutamate-induced ion transport and volume responses in primary astrocyte cultures." *Abstract—J. Physiol. (Paris)*, vol. 82, Nos. 4, pp. 294-303 (1987).
Kempski, O. et al., "Glial ion transport and volume control," *Abstract—Ann N.Y. Acad. Sci.*, vol. 633, pp. 306-317 (1991).
Walz, W., "Role of Na/K/Cl cotransport in astrocytes," *Abstract—Can. J. Physiol. Pharmacol.*, vol. 70, Suppl., pp. S260-S262 (1992).
Walz, W., "Role of astrocytes in the spreading depression signal between ischemic core and penumbra," *Abstract—Neurosci. Biobehav. Rev.*, vol. 21, No. 2., pp. 135-142 (1997).
Hochman, Daryl W., et al., "Extracellular Chloride and the Maintenance of Epileptiform Activity in Hippocampal Slices," *Abstract—Society for Neuroscience*, vol. 23, Part 2., p. 2425 (1997).
Sinha, S.R., et al., "Effects of Furosemide on Normal and Epileptiform Evoked Activity in Area CA1 of Guinea Pig Hippocampal Slice," *Abstract—Society for Neuroscience*, vol. 23. Part 2., p. 2425 (1997).
"Treatment of a Prolonged Migrainous Aura with Intravenous Furosemide", Rosen, T.D., Sep. 2000, Neurology:55, 732-733.
"Acetazolamide Testing of Cerebral Vasodilator Capacity Provokes "Vascular" but not Tension Headaches", Shirai et al., abstract, The Journal of Head and Face Pain, vol. 36, Issue. 10 p. 589, Nov. 1996.
Strategies for Optimizing Migraine Management, Proceedings From a CME Teleconference Series, Sep. 10-14, 2001, pp. 1-26, especially p. 8, para. 5).
"The Migraineur's Guide to Migraine, http://www.headachecare.com", 2000.
Read, S.J., et al., "Furosemide inhibits regenerative cortical spreading depression in anaesthetized cats", *Cephalalgia*, vol. 17, pp. 826-832 (1997).

Mathew, Ninan T., et al., "Coexistence of migraine and idiopathic intracranial hypertension without papilledema", *Neurologyl*, vol. 46, pp. 1226-1230 (May 1996).
Welch, K.M.A., M.D., "Pathogenesis of Migraine", *Seminars in Neurology*, vol. 17, No. 4, pp. 335-341 (1997).
Hesdorffer, D.C., et al., "Severe, Uncontrolled Hypertension and Adult-Onset Seizures: A Case-Control Study in Rochester, Minnesota," *Epilepsia*, vol. 37, No. 8, pp. 736-741 (1996).
"Treatment of Convulsive Ecalmpsia Crisis by Therapeutic Combination; Diazepam, Dihydralazine, Furosemide", 1971, Ngohou-Bonevat et al, Bulletin De La Federation Des Societes De Gynecologie et a D Obstetrique De Langue Francaise.
"Treatment of Hyponatraemic Seizures with Intravenous 29.2% Saline", Worthley et al, 1986, Br. Med. J, vol. 292, pp. 168-170.
"Volumne-sensitive release of taurine from cultured astrocytes: properties and mechanism", Pasantes-Morales et al., 1990, Glia, 3(5), 427-32, Abstract.
Hochman, Daryl W., et al., "Dissociation of Synchronization and Excitability in Furosemide Blockade of Epileptiform Activity," *Science*, vol. 270. pp. 99-102 (Oct. 6, 1995).
Snow, Robert W., et al., "Electrophysiological and Optical Changes in Slice of Rat Hippocampus During Spreading Depression," *Journal of Neurophysiology*, vol. 50, No. 3, pp. 561-572 (Sep. 1983).
Brazil, Carl W., et al., "Advances in the Medical Treatment of Epilepsy," *Annu. Rev. Med.*, vol. 49, pp. 135-162 (1998).
Parsons, Andrew A., "Recent Advances in Mechanisms of Spreading Depression," *Current Opinion in Neurology*, vol. 11, pp. 227-231 (1998).
Jeffreys, John G.R., "Mechanisms and Experimental Models of Seizure Generation," *Current Opinion in Neurology*, vol. 11, pp. 123-127 (1998).
Hochman, Daryl W., Ph.C., "Intrinsic Optical Changes in Neuronal Tissue," *Neurosurgery Clinics of North America*, vol. 8, No. 3, pp. 393-412 (Jul. 1997).
Haglund, Michael M., M.D., Ph.D., et al., "Enhanced Optical Imaging of Human Gliomas and Tumor Margins," *Neurosurgery*, vol. 38, No. 2, pp. 308-317 (Feb. 1996).
Haglund, Michael M., M.D., Ph.D., et al., "Enhanced Optical Imaging of Rat Gliomas and Tumor Margins," *Neurosurgery*, vol. 35, No. 5, pp. 930-941 (Nov. 1994).
Haglund, Michael M., et al., "Optical Imaging of Epileptiform and Functional Activity in Human Cerebral Cortex," *Nature*, vol. 358, pp. 668-671 (Aug. 1992).
Mathew, Ninan T., M.D., et al., "Coexistence of Migraine and Idiopathic Intracranial Hypertension Without Papilledema," *Neurology*, vol. 46, pp. 1226-1230 (May 1996).
Read, S.J., et al., "Furosemide Inhibits Regenerative Cortical Spreading Depression in Anaesthetized Cats," *Cephalalgia*, vol. 17, pp. 826-832 (1997).
Schwartzkroin, Philip A., et al., "Osmolarity, Ionic Flux, and Changes in Brain Excitability," *Epilepsy Research*, vol. 32, pp. 275-285 (1998).
Carter, C.H., "Status Epilepticus Treated by Intravenous Urea," *Epilepsia*, vol. 3, pp. 198-200 (1962).
Reed, Donal J., et al., "The Effect of Hypertonic Urea Solution on Electroshock Seizure Threshold and Eletrolyte Distribution in Rats," *Reed and Woodbury*, vol. 146, pp. 154-159 (1964).
Lowenstein, Daniel H., M.D., et al., "Status Epilepticus," *The New England Journal of Medicine*, vol. 338, No. 14, pp. 970-976 (Apr. 2, 1998).
Upton, Neil, "Mechanisms of Action of New Antiepileptic Drugs: Rational Design and Serendipitous Findings," *TiPS*, vol. 15, pp. 456-463 (Dec. 1994).
Macdonald, Robert L., et al., "Mechanisms of Action of New Antiepileptic Drugs," *Current Opinion in Neurology*, vol. 10, pp. 121-128 (1997).
Welch, K.M.A., M.D., "Pathogenesis of Migraine," *Seminars in Neurology*, vol. 17, No. 4, pp. 335-341 (1997).
Welch, K.M.A., M.D., "Current Opinions in Headache Pathogenesis: Introduction and Synthesis," *Current Opinion in Neurology*, vol. 11, pp. 193-197 (1998).
McLeod, M.S., "The Mysterious Etiology of Head Pain." *Medical Sciences Bulletin*, (Jul. 1996).

(56) References Cited

OTHER PUBLICATIONS

Welch, Mike, M.D., "Brain Imaging Studies Support Neuroelectric Etiology of Migraine Aura," *Reuters Health Information*, 2 pages (May 10, 1999)—Abstract.

Welch, K.M., et al., "The Concept of Migraine as a State of Central Neuronal Hyperexcitability," *Neural Clin.*, vol. 8, pp. 817-828 (1990)—Abstract.

Diener, H.C., et al., "Emerging Treatments in Headache," *European Neurology*, vol. 38, No. 3, pp. 167-174 (1997)—Abstract.

Rivera, C., et al., "The $K^+/Cl^-$ Co-Transported KCC2 Renders GABA Hyperpolarizing During Neuronal Maturation," *Nature*, vol. 397, No. 6716, pp. 251-255 (Jan. 21, 1999)—Abstract.

Lambert, G.A., et al., "Cortical Spreading Depression Reduces Dural Blood Flow—A Possiboe Mechanism for Migraine Pain?" *Cephalalgia*, vol. 14., No. 6, pp. 430-436 (Dec. 1994).

Obrenovitch, T.P., et al., "Inhibition of Cortical Spreading Depression by L-701, 324, A Novel Antagonist at the Glycine Site of the N-Methyl-D-Aspartate Receptor Complex." *British Journal of Pharmacology*, vol. 117., No. 5, pp. 931-937 (Mar. 1997).

Welch, K.M.A., M.D., "Cortical Hyperexcitability Seen as Mechanism for Migraine With Aura," *Reuters Health Information Bulletin*, Jun. 20, 1997.

Borchard et al., European Journal of Pharmaceutical Sciences, vol. 2, No. 1-2, p. 177, Abstract Only (1994).

Extended European Search Report for European Application No. 10180060.5-2107, dated Apr. 20, 2011.

Feit, et al., Purification of Proteins of the Na/Cl Cotransporter from Membranes of Ehrlich Ascites Cells Using a Bumetanide-Sepharose Affinity Column, Journal of Membrane Biology, vol. 103, pp. 135-147, (1988).

Ellory, et al., "The Human Erythrocyte Cl-Dependent Na-K Cotransport System as a Possible Model for Studying the Action of Loop Diretics", British Journal Pharmacology, vol. 75, pp. 183-188, (1982).

Merkel, et al., "Selektive Reduktion von Imiden mit Funktionellen Gruppen", Liebigs Ann. Chem., pp. 461-469, (1979).

Mork, et al., "Furosemide Prodrugs: Synthesis, Enzymatic Hydrolysis and Solubility of Various Furosemide Esters", International Journal of Pharmaceutics—Elsevier, pp. 163-169, (1990).

Petzinger, et al. Interaction of Bumetanide Derivatives with Hepatocellular Bile Acid Uptake, American Journal of Physiology, vol. 265, No. 5, pp. G942-G954, (1993).

Schlatter, et al., "Effect of 'High Ceiling' Diuretics on Active Salt Transport in the Cortical Thick Ascending Limb of Henle's Loop of Rabbit Kidney", Pflugers Archiv., vol. 369, pp. 210-217, (1983).

Shani, J., et al., Structure Activity Correlation for Diuretic Furosemide Congeners, Pharmacology 26: p. 172-180 (1983).

Singapore Search Report and Written Opinion for Singapore Patent Application No. 200802865-6, mailed Sep. 28, 2009.

Collins, et al. (1998) *FASEB Journal* 12(2): 221-230.

Cragoe, et al. (1982) *Journal of Medicinal Chemistry* 25(5): 567-579.

Ellory & Steward (1982) *Br. J. Parmac.* 75: 183-188.

Hochman, et al. (1995) *Science* 270: 99-102.

Inoue, et al. (1989) *European Journal of Pharmacology* 166(1): 101-106.

Larson and Spring (1983) *J. Membrane Biol.* 74: 123-129, 128.

Mathew, et al. (1996) *Neurology* 46(5): 1226-1230.

Misiuk, et al. (1981) *Zh Nevropatol Psikhiatr Im S S Korsakova.* 81(8): 1149-1152.

Mørk, et al. (1990) *International Journal of Pharmaceutics* 60: 163-190, 164; Lüddens, et al. (1998) *European Journal of Pharmacology* 344: 269-277.

Palfrey and Leung (1993) *Am J Phyiol Cell Physiol* 264: C1270-C1277 [Abstract].

Pinegin, et al. (1983) *Zh Nevropatol Psikhiatr Im S S Korsakova.* 83(5): 675-677 [Abstract].

Puschett (1994) "Pharmacological classification and renal actions of diuretics." *Cardiology* 84(Suppl 2): 4-13 [Abstract].

Read, et al. (1997) *Cephalagia* 17(8): 826-832.

Shani, et al. (1983) *Pharmacology* 26: 172-180 [Abstract].

Society for Neuroscience (1997) [Abstract No. 943.3].

Society for Neuroscience (1998) [Abstract No. 476.5].

Suescun, et al. (1998) Acta Cryst. C54: 1911-1915.

Wittner, et al. (1987) Pflugers Arch. (European Journal of Physiology) 408(1): 54-62 [Abstract].

\* cited by examiner

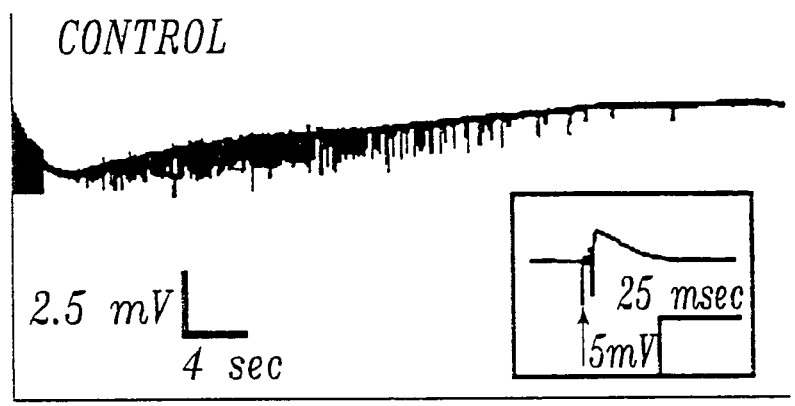
Fig. 1A
Fig. 1A1

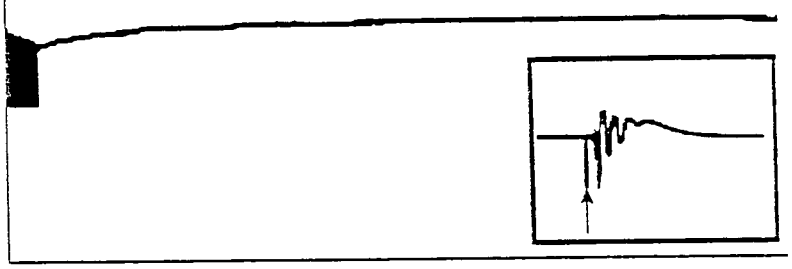
*Fig. 1B*
*Fig. 1B1*

Fig. 1C1

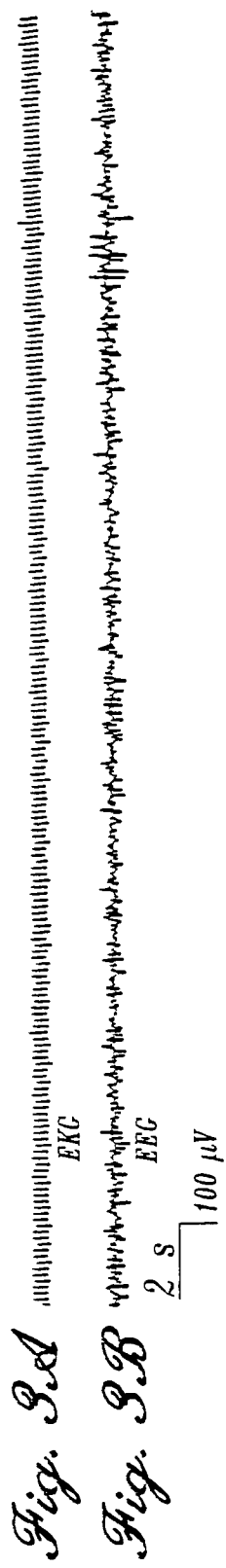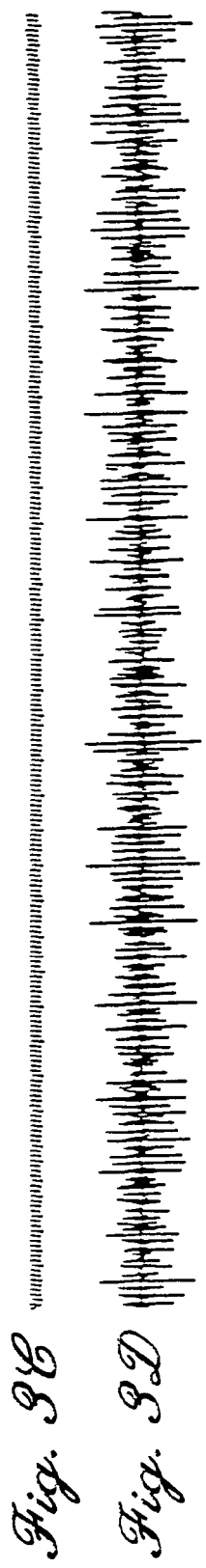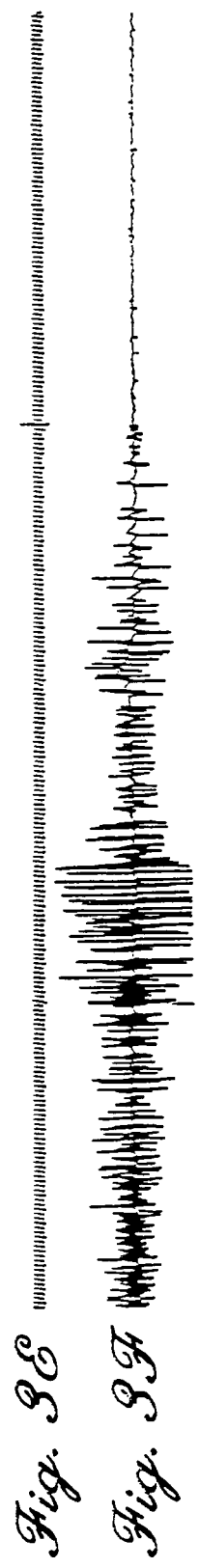
Fig. 3A
Fig. 3B
Fig. 3C
Fig. 3D
Fig. 3E
Fig. 3F
Fig. 3G
Fig. 3H

```
                        SEQUENCE LISTING

<160> NUMBER OF SEQ ID NOS: 2

<210> SEQ ID NO 1
<211> LENGTH: 1212
<212> TYPE: PRT
<213> ORGANISM: Human

<400> SEQUENCE: 1

Met Glu Pro Arg Pro Thr Ala Pro Ser Ser Gly Ala Pro Gly Leu Ala
 1               5                  10                  15

Gly Val Gly Glu Thr Pro Ser Ala Ala Ala Leu Ala Ala Ala Arg Val
                20                  25                  30

Glu Leu Pro Gly Thr Ala Val Pro Ser Val Pro Glu Asp Ala Ala Pro
            35                  40                  45

Ala Ser Arg Asp Gly Gly Val Arg Asp Glu Gly Pro Ala Ala Ala
        50                  55                  60

Gly Asp Gly Leu Gly Arg Pro Leu Gly Pro Thr Pro Ser Gln Ser Arg
65                  70                  75                  80

Phe Gln Val Asp Leu Val Ser Glu Asn Ala Gly Arg Ala Ala Ala Ala
                85                  90                  95

Ala Ala Ala Ala Ala Ala Ala Ala Ala Ala Gly Ala Gly Ala Gly
                100                 105                 110

Ala Lys Gln Thr Pro Ala Asp Gly Glu Ala Ser Gly Glu Ser Glu Pro
            115                 120                 125

Ala Lys Gly Ser Glu Glu Ala Lys Gly Arg Phe Arg Val Asn Phe Val
        130                 135                 140

Asp Pro Ala Ala Ser Ser Ser Ala Glu Asp Ser Leu Ser Asp Ala Ala
145                 150                 155                 160

Gly Val Gly Val Asp Gly Pro Asn Val Ser Phe Gln Asn Gly Gly Asp
                165                 170                 175

Thr Val Leu Ser Glu Gly Ser Ser Leu His Ser Gly Gly Gly Gly
            180                 185                 190

Ser Gly His His Gln His Tyr Tyr Tyr Asp Thr His Thr Asn Thr Tyr
        195                 200                 205

Tyr Leu Arg Thr Phe Gly His Asn Thr Met Asp Ala Val Pro Arg Ile
    210                 215                 220

Asp His Tyr Arg His Thr Ala Ala Gln Leu Gly Glu Lys Leu Leu Arg
225                 230                 235                 240

Pro Ser Leu Ala Glu Leu His Asp Glu Leu Glu Lys Glu Pro Phe Glu
                245                 250                 255
```

```
Asp Gly Phe Ala Asn Gly Glu Glu Ser Thr Pro Thr Arg Asp Ala Val
            260                 265                 270

Val Thr Tyr Thr Ala Glu Ser Lys Gly Val Val Lys Phe Gly Trp Ile
        275                 280                 285

Lys Gly Val Leu Val Arg Cys Met Leu Asn Ile Trp Gly Val Met Leu
    290                 295                 300

Phe Ile Arg Leu Ser Trp Ile Val Gly Gln Ala Gly Ile Gly Leu Ser
305                 310                 315                 320

Val Leu Val Ile Met Met Ala Thr Val Thr Thr Ile Thr Gly Leu
            325                 330                 335

Ser Thr Ser Ala Ile Ala Thr Asn Gly Phe Val Arg Gly Gly Gly Ala
            340                 345                 350

Tyr Tyr Leu Ile Ser Arg Ser Leu Gly Pro Glu Phe Gly Gly Ala Ile
            355                 360                 365

Gly Leu Ile Phe Ala Phe Ala Asn Ala Val Ala Val Ala Met Tyr Val
        370                 375                 380

Val Gly Phe Ala Glu Thr Val Val Glu Leu Leu Lys Glu His Ser Ile
385                 390                 395                 400

Leu Met Ile Asp Glu Ile Asn Asp Ile Arg Ile Ile Gly Ala Ile Thr
                405                 410                 415

Val Val Ile Leu Leu Gly Ile Ser Val Ala Gly Met Glu Trp Glu Ala
            420                 425                 430

Lys Ala Gln Ile Val Leu Leu Val Ile Leu Leu Ala Ile Gly Asp
            435                 440                 445

Phe Val Ile Gly Thr Phe Ile Pro Leu Glu Ser Lys Lys Pro Lys Gly
    450                 455                 460

Phe Phe Gly Tyr Lys Ser Glu Ile Phe Asn Glu Asn Phe Gly Pro Asp
465                 470                 475                 480

Phe Arg Glu Glu Glu Thr Phe Phe Ser Val Phe Ala Ile Phe Phe Pro
                485                 490                 495

Ala Ala Thr Gly Ile Leu Ala Gly Ala Asn Ile Ser Gly Asp Leu Ala
            500                 505                 510

Asp Pro Gln Ser Ala Ile Pro Lys Gly Thr Leu Leu Ala Ile Leu Ile
        515                 520                 525

Thr Thr Leu Val Tyr Val Gly Ile Ala Val Ser Val Gly Ser Cys Val
        530                 535                 540

Val Arg Asp Ala Thr Gly Asn Val Asn Asp Thr Ile Val Thr Glu Leu
545                 550                 555                 560

Thr Asn Cys Thr Ser Ala Ala Cys Lys Leu Asn Phe Asp Phe Ser Ser
                565                 570                 575

Cys Glu Ser Ser Pro Cys Ser Tyr Gly Leu Met Asn Asn Phe Gln Val
            580                 585                 590

Met Ser Met Val Ser Gly Phe Thr Pro Leu Ile Ser Ala Gly Ile Phe
        595                 600                 605

Ser Ala Thr Leu Ser Ser Ala Leu Ala Ser Leu Val Ser Ala Pro Lys
        610                 615                 620

Ile Phe Gln Ala Leu Cys Lys Asp Asn Ile Tyr Pro Ala Phe Gln Met
625                 630                 635                 640

Phe Ala Lys Gly Tyr Gly Lys Asn Asn Glu Pro Leu Arg Gly Tyr Ile
                645                 650                 655

Leu Thr Phe Leu Ile Ala Leu Gly Phe Ile Leu Ile Ala Glu Leu Asn
            660                 665                 670

Val Ile Ala Pro Ile Ile Ser Asn Phe Phe Leu Ala Ser Tyr Ala Leu
```

-continued

```
            675                 680                 685
Ile Asn Phe Ser Val Phe His Ala Ser Leu Ala Lys Ser Pro Gly Trp
690                 695                 700
Arg Pro Ala Phe Lys Tyr Tyr Asn Met Trp Ile Ser Leu Leu Gly Ala
705                 710                 715                 720
Ile Leu Cys Cys Ile Val Met Phe Val Ile Asn Trp Trp Ala Ala Leu
            725                 730                 735
Leu Thr Tyr Val Ile Val Leu Gly Leu Tyr Ile Tyr Val Thr Tyr Lys
                740                 745                 750
Lys Pro Asp Val Asn Trp Gly Ser Ser Thr Gln Ala Leu Thr Tyr Leu
    755                 760                 765
Asn Ala Leu Gln His Ser Ile Arg Leu Ser Gly Val Glu Asp His Val
    770                 775                 780
Lys Asn Phe Arg Pro Gln Cys Leu Val Met Thr Gly Ala Pro Asn Ser
785                 790                 795                 800
Arg Pro Ala Leu Leu His Leu Val His Asp Phe Thr Lys Asn Val Gly
                805                 810                 815
Leu Met Ile Cys Gly His Val His Met Gly Pro Arg Arg Gln Ala Met
                820                 825                 830
Lys Glu Met Ser Ile Asp Gln Ala Lys Tyr Gln Arg Trp Leu Ile Lys
        835                 840                 845
Asn Lys Met Lys Ala Phe Tyr Ala Pro Val His Ala Asp Asp Leu Arg
    850                 855                 860
Glu Gly Ala Gln Tyr Leu Met Gln Ala Ala Gly Leu Gly Arg Met Lys
865                 870                 875                 880
Pro Asn Thr Leu Val Leu Gly Phe Lys Lys Asp Trp Leu Gln Ala Asp
                885                 890                 895
Met Arg Asp Val Asp Met Tyr Ile Asn Leu Phe His Asp Ala Phe Asp
                900                 905                 910
Ile Gln Tyr Gly Val Val Ile Arg Leu Lys Glu Gly Leu Asp Ile
        915                 920                 925
Ser His Leu Gln Gly Gln Glu Glu Leu Leu Ser Ser Gln Glu Lys Ser
    930                 935                 940
Pro Gly Thr Lys Asp Val Val Ser Val Glu Tyr Ser Lys Lys Ser
945                 950                 955                 960
Asp Leu Asp Thr Ser Lys Pro Leu Ser Glu Lys Pro Ile Thr His Lys
                965                 970                 975
Val Glu Glu Glu Asp Gly Lys Thr Ala Thr Gln Pro Leu Leu Lys Lys
                980                 985                 990
Glu Ser Lys Gly Pro Ile Val Pro Leu Asn Val Ala Asp Gln Lys Leu
        995                 1000                1005
Leu Glu Ala Ser Thr Gln Phe Gln Lys Lys Gln Gly Lys Asn Thr Ile
    1010                1015                1020
Asp Val Trp Trp Leu Phe Asp Asp Gly Gly Leu Thr Leu Leu Ile Pro
1025                1030                1035                1040
Tyr Leu Leu Thr Thr Lys Lys Lys Trp Lys Asp Cys Lys Ile Arg Val
                1045                1050                1055
Phe Ile Gly Gly Lys Ile Asn Arg Ile Asp His Asp Arg Arg Ala Met
                1060                1065                1070
Ala Thr Leu Leu Ser Lys Phe Arg Ile Asp Phe Ser Asp Ile Met Val
        1075                1080                1085
Leu Gly Asp Ile Asn Thr Lys Pro Lys Lys Glu Asn Ile Ile Ala Phe
        1090                1095                1100
```

-continued

Glu Glu Ile Ile Glu Pro Tyr Arg Leu His Glu Asp Asp Lys Glu Gln
1105                1110                1115                1120

Asp Ile Ala Asp Lys Met Lys Glu Asp Glu Pro Trp Arg Ile Thr Asp
            1125                1130                1135

Asn Glu Leu Glu Leu Tyr Lys Thr Lys Thr Tyr Arg Gln Ile Arg Leu
        1140                1145                1150

Asn Glu Leu Leu Lys Glu His Ser Ser Thr Ala Asn Ile Ile Val Met
    1155                1160                1165

Ser Leu Pro Val Ala Arg Lys Gly Ala Val Ser Ser Ala Leu Tyr Met
1170                1175                1180

Ala Trp Leu Glu Ala Leu Ser Lys Asp Leu Pro Pro Ile Leu Leu Val
1185                1190                1195                1200

Arg Gly Asn His Gln Ser Val Leu Thr Phe Tyr Ser
                1205                1210

<210> SEQ ID NO 2
<211> LENGTH: 6891
<212> TYPE: DNA
<213> ORGANISM: Human

<400> SEQUENCE: 2

```
ggtggcctct gtggccgtcc aggctagcgg cggcccgcag gcggcgggga gaaagactct      60
ctcacctggt cttgcggctg tggccaccgc cggccagggg tgtggagggc gtgctgccgg     120
agacgtccgc cgggctctgc agttccgccg ggggtcgggc agctatggag ccgcggccca     180
cggcgccctc ctccggcgcc ccgggactgg ccggggtcgg ggagacgccg tcagccgctg     240
cgctggccgc agccagggtg gaactgcccg gcacggctgt gccctcggtg ccggaggatg     300
ctgcgcccgc gagccgggac ggcggcgggg tccgcgatga gggccccgcg gcggccgggg     360
acgggctggg cagacccttg ggcccacccc cgagccagag ccgtttccag gtggacctgg     420
tttccgagaa cgccgggcgg gccgctgctg cggcggcggc ggcggcggcg cagcggcgg     480
cggctggtgc tggggcgggg gccaagcaga ccccccgcgga cggggaagcc agcggcgaga     540
gcgagccggc taaaggcagc gaggaagcca agggccgctt ccgcgtgaac ttcgtggacc     600
cagctgcctc ctcgtcggct gaagacagcc tgtcagatgc tgccggggtc ggagtcgacg     660
ggcccaacgt gagcttccag aacgcgcggg acacggtgct gagcgagggc agcagcctgc     720
actccggcgg cggcggcggc agtgggcacc accagcacta ctattatgat acccacacca     780
acacctacta cctgcgcacc ttcggccaca caccatggga cgctgtgccc aggatcgatc     840
actaccggca cacagccgcg cagctgggcg agaagctgct ccggcctagc ctggcggagc     900
tccacgacga gctggaaaag gaaccttttg aggatggctt tgcaaatggg gaagaaagta     960
ctccaaccag agatgctgtg gtcacgtata ctgcagaaag taaggagtc gtgaagtttg    1020
gctggatcaa gggtgtatta gtacgttgta tgttaaacat ttggggtgtg atgcttttca    1080
ttagattgtc atggattgtg ggtcaagctg aataggtct atcagtcctt gtaataatga    1140
tggccactgt tgtgacaact atcacaggat tgtctacttc agcaatagca actaatggat    1200
ttgtaagagg aggaggagca tattatttaa tatctagaag tctagggcca gaatttggtg    1260
gtgcaattgg tctaatcttc gcctttgcca acgctgttgc agttgctatg tatgtggttg    1320
gatttgcaga aaccgtggtg gagttgctta aggaacattc catacttatg atagatgaaa    1380
tcaatgatat ccgaattatt ggagccatta cagtcgtgat tcttttaggt atctcagtag    1440
ctggaatgga gtgggaagca aaagctcaga ttgttctttt ggtgatccta cttcttgcta    1500
ttggtgattt cgtcatagga acatttatcc cactggagag caagaagcca aagggttttt    1560
```

```
ttggttataa atctgaaata tttaatgaga actttgggcc cgattttcga gaggaagaga      1620
cttctttttc tgtatttgcc atcttttttc ctgctgcaac tggtattctg gctggagcaa      1680
atatctcagg tgatcttgca gatcctcagt cagccatacc caaaggaaca ctcctagcca      1740
ttttaattac tacattggtt tacgtaggaa ttgcagtatc tgtaggttct tgtgttgttc      1800
gagatgccac tggaaacgtt aatgacacta tcgtaacaga gctaacaaac tgtacttctg      1860
cagcctgcaa attaaacttt gattttcat cttgtgaaag cagtccttgt tcctatggcc       1920
taatgaacaa cttccaggta atgagtatgg tgtcaggatt tacaccacta atttctgcag      1980 gtatatttc agccactctt tcttcagcat tagcatccct agtgagtgct cccaaaatat       2040
ttcaggctct atgtaaggac aacatctacc cagctttcca gatgtttgct aaaggttatg      2100
ggaaaaataa tgaacctctt cgtggctaca tcttaacatt cttaattgca cttggattca     2160
tcttaattgc tgaactgaat gttattgcac caattatctc aaacttcttc cttgcatcat      2220
atgcattgat caattttca gtattccatg catcacttgc aaaatctcca ggatggcgtc       2280
ctgcattcaa atactacaac atgtggatat cacttcttgg agcaattctt tgttgcatag      2340
taatgttcgt cattaactgg tgggctgcat tgctaacata tgtgatagtc cttgggctgt      2400
atatttatgt tacctacaaa aaaccagatg tgaattgggg atcctctaca caagccctga     2460
cttacctgaa tgcactgcag cattcaattc gtctttctgg agtggaagac cacgtgaaaa     2520
actttaggcc acagtgtctt gttatgacag gtgctccaaa ctcacgtcca gctttacttc      2580
atcttgttca tgatttcaca aaaaatgttg gtttgatgat ctgtggccat gtacatatgg     2640
gtcctcgaag acaagccatg aaagagatgt ccatcgatca agccaaatat cagcgatggc     2700
ttattaagaa caaaatgaag gcattttatg ctccagtaca tgcagatgac ttgagagaag     2760
gtgcacagta tttgatgcag gctgctggtc ttggtcgtat gaagccaaac acacttgtcc     2820
ttggatttaa gaaagattgg ttgcaagcag atatgaggga tgtggatatg tatataaact      2880
tatttcatga tgcttttgac atacaatatg gagtagtggt tattcgccta aaagaaggtc      2940
tggatatatc tcatcttcaa ggacaagaag aattattgtc atcacaagag aaatctcctg      3000
gcaccaagga tgtggtagta agtgtggaat atagtaaaaa gtccgattta gatacttcca     3060
aaccactcag tgaaaaacca attacacaca aagttgagga agaggatggc aagactgcaa      3120
ctcaaccact gttgaaaaaa gaatccaaag gccctattgt gcctttaaat gtagctgacc     3180
aaaagcttct tgaagctagt acacagtttc agaaaaaaca aggaaagaat actattgatg      3240
tctggtggct ttttgatgat ggaggtttga cctattgat accttacctt ctgacgacca      3300
agaaaaaatg gaaagactgt aagatcagag tattcattgg tggaaagata aacagaatag      3360
accatgaccg gagagcgatg gctactttgc ttagcaagtt ccggatagac tttctgata    3420 tcatggttct aggagatatc aataccaaac caaagaaaga aaatattata gcttttgagg      3480
aaatcattga gccatacaga cttcatgaag atgataaaga gcaagatatt gcagataaaa      3540
tgaaagaaga tgaaccatgg cgaataacag ataatgagct tgaactttat aagaccaaga     3600
cataccggca gatcaggtta aatgagttat taaaggaaca ttcaagcaca gctaatatta    3660
ttgtcatgag tctcccagtt gcacgaaaag gtgctgtgtc tagtgctctc tacatggcat     3720
ggttagaagc tctatctaag gacctaccac caatcctcct agttcgtggg aatcatcaga     3780
gtgtccttac cttctattca taaatgttct atacagtgga cagccctcca gaatggtact     3840
tcagtgccta gtgtagtaac tgaaatcttc aatgacacat taacatcaca atggcgaatg     3900
gtgacttttc tttcacgatt tcattaattt gaaagcacac aggaaagttg ctccattgat     3960
```

```
aacgtgtatg gagacttcgg ttttagtcaa ttccatatct caatcttaat ggtgattctt    4020
ctctgttgaa ctgaagtttg tgagagtagt tttcctttgc tacttgaata gcaataaaag    4080
cgtgttaact ttttgattga tgaaagaagt acaaaaagcc tttagccttg aggtgccttc    4140
tgaaattaac caaatttcat ccatatatcc tcttttataa acttatagaa tgtcaaactt    4200
tgccttcaac tgttttatt tctagtctct tccactttaa aacaaaatga acactgcttg    4260
tcttcttcca ttgaccattt agtgttgagt actgtatgtg ttttgttaat tctataaagg    4320
tatctgttag atattaaagg tgagaattag ggcaggttaa tcaaaatgg ggaagggaa     4380 atggtaacca aaaagtaacc ccatggtaag gtttatatga gtatatgtga atatagagct    4440
aggaaaaaaa gcccccccaa ataccttttt aacccctctg attggctatt attactatat    4500
ttattattat ttattgaaac cttagggaag attgaagatt catcccatac ttctatatac    4560
catgcttaaa aatcacgtca ttctttaaac aaaaatactc aagatcattt atatttattt    4620
ggagagaaaa ctgtcctaat ttagaatttc cctcaaatct gagggacttt taagaaatgc    4680
taacagattt ttctggagga aatttagaca aaacaatgtc atttagtaga atatttcagt    4740
atttaagtgg aatttcagta tactgtacta tcctttataa gtcattaaaa taatgtttca    4800
tcaaatggtt aaatggacca ctggtttctt agagaaatgt ttttaggctt aattcattca    4860
attgtcaagt acacttagtc ttaatacact caggtttgaa cagattattc tgaatattaa    4920
aatttaatcc attcttaata ttttaaaact tttgttaaga aaaactgcca gtttgtgctt    4980
ttgaaatgtc tgttttgaca tcatagtcta gtaaaatttt gacagtgcat atgtactgtt    5040
actaaaagct ttatatgaaa ttattaatgt gaagttttc atttataatt caaggaagga    5100
tttcctgaaa acatttcaag ggattttatgt ctacatattt gtgtgtgtgt gtgtatatat    5160
atgtaatatg catacacaga tgcatatgtg tatatataat gaaatttatg ttgctggtat    5220
tttgcatttt aaagtgatca agattcatta ggcaaacttt ggtttaagta aacatatgtt    5280
caaaatcaga ttaacagata caggtttcat agagaacaaa ggtgatcatt tgaagggcat    5340
gctgtaattt cacacaattt tccagttcaa aaatggagaa tacttcgcct aaaatactgt    5400
taagtgggtt aattgataca agtttctgtg gtggaaaatt tatgcaggtt ttcacgaatc    5460
cttttttttt ttttttttt ttttttgagac ggagtcttgc tctgttgcca cgctggaatg    5520
cagtaacgtg atcttggctc actgcgacct ccacctcccc agttcaagcg attctcctgc    5580
ctcagcctcc ctagtagctg ggactacggg tgcacgccac catgcccagc taattttgt    5640 attttgagta gagacagggt ttcaccgtgt tggctaggat ggtgtctatc tcttgacctt    5700
gtgatccacc cgcctcagcc tcccagagtg ctgggattac aggtgcgagc cactgcgcct    5760
ggctggtttt catgaatctt gatagacatc tataacgtta ttattttcag tggtgtgcag    5820
catttttgct tcatgagtat gacctaggta tagagatctg ataacttgaa ttcagaatat    5880
taagaaaatg aagtaactga ttttctaaaa aaaaaaaaa aaaaatttc tacattataa    5940 ctcacagcat tgttccattg caggttttgc aatgtttggg ggtaaagaca gtagaaatat    6000
tattcagtaa acaataatgt gtgaactttt aagatggata ataggggcatg gactgagtgc    6060 tgctatcttg aaatgtgcac aggtacactt accttttttt ttttttttt taagttttc    6120 ccattcagga aaacaacatt gtgatctgta ctacaggaac caaatgtcat gcgtcataca    6180
tgtgggtata aagtacataa aatatatcta actattcata atgtggggtg ggtaatactg    6240
tctgtgaaat aatgtaagaa gcttttcact taaaaaaaat gcattacttt cacttaacac    6300
tagacaccag gtcgaaaatt ttcaaggtta tagtacttat ttcaacaatt cttagagatg    6360
```

-continued

```
ctagctagtg ttgaagctaa aaatagcttt atttatgctg aattgtgatt tttttatgcc    6420 aaatttttt  tagttctaat cattgatgat agcttggaaa taaataatta tgccatggca    6480
tttgacagtt cattattcct ataagaatta aattgagttt agagagaatg gtggtgttga    6540
gctgattatt aacagttact gaaatcaaat atttatttgt tacattattc catttgtatt    6600
ttaggtttcc ttttacattc tttttatatg cattctgaca ttacatattt tttaagacta    6660
tggaaataat ttaaagattt aagctctggt ggatgattat ctgctaagta agtctgaaaa    6720
tgtaatattt tgataatact gtaatatacc tgtcacacaa atgcttttct aatgttttaa    6780
ccttgagtat tgcagttgct gctttgtaca gaggttactg caataaagga agtggattca    6840
ttaaacctat ttaatgtcca aaaaaaaaaa aaaaaaaaa aaaaaaaaaa a              6891
```

METHODS AND COMPOSITIONS FOR THE TREATMENT OF NEUROPATHIC PAIN AND NEUROPSYCHIATRIC DISORDERS

REFERENCE TO RELATED APPLICATIONS

This application is a continuation-in-part of U.S. patent application Ser. No. 10/056,528, filed Jan. 23, 2002, now U.S. Pat. No. 7,214,711, which claims priority under 35 U.S.C. §119(e) to U.S. Patent Application No. 60/263,830, filed Jan. 23, 2001, and is a continuation-in-part of U.S. patent application Ser. No. 09/470,637, filed Dec. 22, 1999, now U.S. Pat. No. 6,495,601, which claims priority under 35 U.S.C. §119(e) to U.S. Patent Application 60/113,620, filed Dec. 23, 1998.

TECHNICAL FIELD OF THE INVENTION

The present invention relates to methods and compositions for treating selected conditions of the central and peripheral nervous systems employing non-synaptic mechanisms. More specifically, the present invention relates to methods and compositions for treating neuropathic pain and neuropsychiatric disorders by administering agents that modulate expression and/or activity of sodium-potassium-chloride co-transporters.

BACKGROUND OF THE INVENTION

Neuropathic pain and nociceptive pain differ in their etiology, pathophysiology, diagnosis and treatment. Nociceptive pain occurs in response to the activation of a specific subset of peripheral sensory neurons, the nociceptors. It is generally acute (with the exception of arthritic pain), self-limiting and serves a protective biological function by acting as a warning of on-going tissue damage. It is typically well localized and often has an aching or throbbing quality. Examples of nociceptive pain include post-operative pain, sprains, bone fractures, burns, bumps, bruises, inflammation (from an infection or arthritic disorder), obstructions and myofascial pain. Nociceptive pain can usually be treated with opioids and non-steroidal anti-inflammatory drugs (NSAIDS).

Neuropathic pain is a common type of chronic, non-malignant, pain, which is the result of an injury or malfunction in the peripheral or central nervous system and serves no protective biological function. It is estimated to affect more than 1.6 million people in the U.S. population. Neuropathic pain has many different etiologies, and may occur, for example, due to trauma, diabetes, infection with herpes zoster (shingles), HIV/AIDS, late-stage cancer, amputation (including mastectomy), carpal tunnel syndrome, chronic alcohol use, exposure to radiation, and as an unintended side-effect of neurotoxic treatment agents, such as certain anti-HIV and chemotherapeutic drugs.

In contrast to nociceptive pain, neuropathic pain is frequently described as "burning", "electric", "tingling" or "shooting" in nature. It is often characterized by chronic allodynia (defined as pain resulting from a stimulus that does not ordinarily elicit a painful response, such as light touch) and hyperalgesia (defined as an increased sensitivity to a normally painful stimulus), and may persist for months or years beyond the apparent healing of any damaged tissues.

Neuropathic pain is difficult to treat. Analgesic drugs that are effective against normal pain (e.g., opioid narcotics and non-steroidal anti-inflammatory drugs) are rarely effective against neuropathic pain. Similarly, drugs that have activity in neuropathic pain are not usually effective against nociceptive pain. The standard drugs that have been used to treat neuropathic pain appear to often act selectively to relieve certain symptoms but not others in a given patient (for example, relief of allodynia, but not hyperalgesia). For this reason, it has been suggested that successful therapy may require the use of multiple different combinations of drugs and individualized therapy (see, for example, Bennett, *Hosp. Pract.* (Off Ed). 33:95-98, 1998). Treatment agents typically employed in the management of neuropathic pain include tricylic antidepressants (for example, amitriptyline, imipramine, desimipramine and clomipramine), systemic local anesthetics, and anti-convulsants (such as phenyloin, carbamazepine, valproic acid, clonazepam and gabapentin).

Many anti-convulsants originally developed for the treatment of epilepsy and other seizure disorders have found application in the treatment of non-epileptic conditions, including neuropathic pain, mood disorders (such as bipolar affective disorder), and schizophrenia (for a review of the use of anti-epileptic drugs in the treatment of non-epileptic conditions, see Rogawski and Loscher, *Nat. Medicine,* 10:685-692, 2004). It has thus been suggested that epilepsy, neuropathic pain and affective disorders have a common pathophysiological mechanism (Rogawski & Loscher, ibid; Ruscheweyh & Sandkuhler, *Pain* 105:327-338, 2003), namely a pathological increase in neuronal excitability, with a corresponding inappropriately high frequency of spontaneous firing of neurons. However, only some, and not all, anti-epileptic drugs are effective in treating neuropathic pain, and furthermore such antiepileptic drugs are only effective in certain subsets of patients with neuropathic pain (McCleane, *Expert. Opin. Pharmacother.* 5:1299-1312, 2004).

Epilepsy is characterized by abnormal discharges of cerebral neurons and is typically manifested as various types of seizures. Epileptiform activity is identified with spontaneously occurring synchronized discharges of neuronal populations that can be measured using electrophysiological techniques. This synchronized activity, which distinguishes epileptiform from non-epileptiform activity, is referred to as "hypersynchronization" because it describes the state in which individual neurons become increasingly likely to discharge in a time-locked manner with one another. Hypersynchronized activity is typically induced in experimental models of epilepsy by either increasing excitatory or decreasing inhibitory synaptic currents, and it was therefore assumed that hyperexcitability per se was the defining feature involved in the generation and maintenance of epileptiform activity. Similarly, neuropathic pain was believed to involve conversion of neurons involved in pain transmission from a state of normal sensitivity to one of hypersensitivity (Costigan & Woolf, *Jnl. Pain* 1:35-44, 2000). The focus on developing treatments for both epilepsy and neuropathic pain has thus been on suppressing neuronal hyperexcitability by either: (a) suppressing action potential generation; (b) increasing inhibitory synaptic transmission; or (c) decreasing excitatory synaptic transmission. However, it has been shown that hypersychronous epileptiform activity can be dissociated from hyperexcitability and that the cation chloride cotransport inhibitor furosemide reversibly blocked synchronized discharges without reducing hyperexcited synaptic responses (Hochman et al. *Science* 270:99-102, 1995).

Both abnormal expression of sodium channel genes (Waxman, *Pain* 6:S133-140, 1999; Waxman et al. *Proc. Natl. Acad. Sci USA* 96:7635-7639, 1999) and pacemaker channels (Chaplan et al. *J. Neurosci.* 23:1169-1178, 2003) are believed to play a role in the molecular basis of neuropathic pain.

The cation-chloride co-transporters (CCCs) are important regulators of neuronal chloride concentration that are believed to influence cell-to-cell communication, and various aspects of neuronal development, plasticity and trauma. The CCC gene family consists of three broad groups: $Na^+$—$Cl^-$ co-transporters (NCCs), $K^+$—$Cl^-$ co-transporters (KCCs) and $Na^+$—$K^+$-$2Cl^-$ co-transporters (NKCCs). Two NKCC isoforms have been identified: NKCC1 is found in a wide variety of secretory epithelia and non-epithelial cells, whereas NKCC2 is principally expressed in the kidney. For a review of NKCC1 structure, function and regulation see, Haas and Forbush, *Annu. Rev. Physiol.* 62:515-534, 2000. Randall et al. have identified two splice variants of the Slc12a2 gene that encodes NKCC1, referred to as NKCC1a and NKCC1b (*Am. J. Physiol.* 273 (*Cell Physiol.* 42):C1267-1277, 1997). The NKCC1a gene has 27 exons, while the splice variant NKCC1b lacks exon 21. The NKCC1b splice variant is expressed primarily in the brain. NKCC1b is believed to be more than 10% more active than NKCC1a, although it is proportionally present in a much smaller amount in the brain than is NKCC1a. It has been suggested that differential splicing of the NKCC1 transcript may play a regulatory role in human tissues (Vibat et al. *Anal. Biochem.* 298:218-230, 2001). Na—K—Cl co-transport in all cell and tissues is inhibited by loop diuretics, including furosemide, bumetanide and benzmetanide.

Na—K-2Cl co-transporter knock-out mice have been shown to have impaired nociception phenotypes as well as abnormal gait and locomotion (Sung et al. *Jnl. Neurosci.* 20:7531-7538, 2000). Delpire and Mount have suggested that NKCC1 may be involved in pain perception (*Ann. Rev. Physiol.* 64:803-843, 2002). Laird et al. recently described studies demonstrating reduced stroking hyperalgesia in NKCC1 knock-out mice compared to wild-type and heterozygous mice (*Neurosci. Letts.* 361:200-203, 2004). However, in this acute pain model no difference in punctuate hyperalgesia was observed between the three groups of mice. Morales-Aza et al. have suggested that, in arthritis, altered expression of NKCC1 and the K—Cl co-transporter KCC2 may contribute to the control of spinal cord excitability and may thus represent therapeutic targets for the treatment of inflammatory pain (*Neurobiol. Dis.* 17:62-69, 2004). Granados-Soto et al. have described studies in rats in which formalin-induced nociception was reduced by administration of the NKCC inhibitors bumetanide, furosemide or piretanide (*Pain* 114:231-238, 2005). While the formalin-induced acute pain model is extensively used, it is believed to have little relevance to chronic pain conditions (Walker et al. *Mol. Med. Today* 5:319-321, 1999). Co-treatment of brain damage induced by episodic alcohol exposure with an NMDA receptor antagonist, non-NMDA receptor and $Ca^{2+}$ channel antagonists together with furosemide has been shown to reduce alcohol-dependent cerebrocortical damage by 75-85%, while preventing brain hydration and electrolyte elevations (Collins et al, *FASEB J.*, 12:221-230, 1998). The authors stated that the results suggest that furosemide and related agents might be useful as neuroprotective agents in alcohol abuse. Willis et al. have published studies indicating that nedocromil sodium, furosemide and bumetanide inhibit sensory nerve activation to reduce the itch and flare responses induced by histamine in human skin in vivo. Espinosa et al. and Ahmad et al. have previously suggested that furosemide might be useful in the treatment of certain types of epilepsy (*Medicina Espanola* 61:280-281, 1969; and *Brit. J. Clin. Pharmacol.* 3:621-625, 1976).

As with epilepsy, the focus of pharmacological intervention in neuropathic pain has been on reducing neuronal hyperexcitability. Most agents currently used to treat neuropathic pain target synaptic activity in excitatory pathways by, for example, modulating the release or activity of excitatory neurotransmitters, potentiating inhibitory pathways, blocking ion channels involved in impulse generation, and/or acting as membrane stabilizers. Conventional agents and therapeutic approaches for the treatment of neuropathic pain and neuropsychiatric disorders thus reduce neuronal excitability and inhibit synaptic firing. One serious drawback of these therapies is that they are nonselective and exert their actions on both normal and abnormal neuronal populations. This leads to negative and unintended side effects, which may affect normal CNS functions, such as cognition, learning and memory, and produce adverse physiological and psychological effects in the treated patient. Common side effects include over-sedation, dizziness, loss of memory and liver damage. There is therefore a continuing need for methods and compositions for treating neuronal disorders that disrupt hypersynchronized neuronal activity without diminishing the neuronal excitability and spontaneous synchronization required for normal functioning of the peripheral and central nervous systems.

SUMMARY OF THE INVENTION

The treatment compositions and methods of the present invention are useful for treating conditions including neuropathic pain and neuropsychiatric disorders, such as bipolar disorders, anxiety, panic attacks, depression, schizophrenia and post-traumatic stress syndrome that are characterized by neuronal hypersynchrony. The inventive compositions and methods may be employed to reduce neuronal hypersynchrony associated with neuropathic pain and/or neuropsychiatric disorders without suppressing neuronal excitability, thereby avoiding the unwanted side effects often associated with agents currently employed for the treatment of neuropathic pain and neuropsychiatric disorders.

The methods and compositions disclosed herein generally involve via non-synaptic mechanisms and modulate, generally reduce, the synchronization of neuronal population activity. The synchronization of neuronal population activity is modulated by manipulating anionic concentrations and gradients in the central and/or peripheral nervous systems. More specifically, the inventive compositions are capable of reducing the effective amount, inactivating, and/or inhibiting the activity of a $Na^+$—$K^+$-$2Cl^-$ (NKCC) co-transporter. Especially preferred treatment agents of the present invention, exhibit a high degree of NKCC co-transporter antagonist activity in cells of the central and/or peripheral nervous system, e.g., glial cells, Schwann cells and/or neuronal cell populations, and exhibit a lesser degree of activity in renal cell populations. In one embodiment, the inventive compositions are capable of reducing the effective amount, inactivating, and/or inhibiting the activity of the co-transporter NKCC1. NKCC1 antagonists are especially preferred treatment agents for use in the inventive methods. NKCC co-transporter antagonists that may be usefully employed in the inventive treatment compositions include, but are not limited to, loop diuretics such as furosemide, bumetanide, ethacrynic acid, torsemide, azosemide, muzolimine, piretanide, tripamide and the like, as well as thiazide and thiazide-like diuretics, such as bendroflumethiazide, benzthiazide, chlorothiazide, hydrochlorothiazide, hydroflumethiazide, methylclothiazide, polythiazide, trichlormethiazide, chlorthalidone, indapamide, metolazone and quinethazone, together with analogs and functional derivatives of such components.

Other treatment agents that may be usefully employed in the inventive compositions and methods include, but are not limited to: antibodies, or antigen-binding fragments thereof, that specifically bind to NKCC1; soluble NKCC1 ligands; small molecule inhibitors of NKCC1; anti-sense oligonucleotides to NKCC1; NKCC1-specific small interfering RNA molecules (siRNA or RNAi); and engineered soluble NKCC1 molecules. Preferably, such antibodies, or antigen-binding fragments thereof, and small molecule inhibitors of NKCC1 specifically bind to the domains of NKCC1 involved in bumetanide binding, as described, for example, in Haas and Forbush II, *Annu. Rev. Physiol.* 62:515-534, 2000. The polypeptide sequence for human NKCC1 is provided in SEQ ID NO: 1, with the corresponding cDNA sequence being provided in SEQ ID NO: 2.

As the methods and treatment agents of the present invention employ "non-synaptic" mechanisms, little or no suppression of neuronal excitability occurs. More specifically, the inventive treatment agents cause little (less than a 1% change compared to pre-administration levels) or no suppression of action potential generation or excitatory synaptic transmission. In fact, a slight increase in neuronal excitability may occur upon administration of certain of the inventive treatment agents. This is in marked contrast to conventional antiepileptic drugs currently used in the treatment of neuropathic pain, which do suppress neuronal excitability. The methods and treatment agents of the present invention affect the synchronization, or relative synchrony, of neuronal population activity. Preferred methods and treatment agents modulate the extracellular anionic chloride concentration and/or the gradients in the central or peripheral nervous system to reduce neuronal synchronization, or relative synchrony, without substantially affecting neuronal excitability.

In one aspect, the present invention relates to methods and agents for relieving neuropathic pain, or the abnormal perception of pain, by affecting or modulating spontaneous hypersynchronized bursts of neuronal activity and the propagation of action potentials or conduction of impulses in certain cells and nerve fibers of the peripheral nervous system, for example, primary sensory afferent fibers, pain fibers, dorsal horn neurons, and supraspinal sensory and pain pathways.

The inventive treatment agents may be employed in combination with other, known, treatment agents, such as those presently used in the treatment of neuropathic pain and/or neuropsychiatric disorders. One of skill in the art will appreciate that the combination of a treatment agent of the present invention with another, known, treatment agent may involve both synaptic and non-synaptic mechanisms.

Treatment compositions and methods of the present invention may be used therapeutically and episodically following the onset of symptoms or prophylactically, prior to the onset of specific symptoms. For example, treatment agents of the present invention can be used to treat existing neuropathic pain or to protect nerves from neurotoxic injury and neuropathic pain secondary to chemotherapy, radiotherapy, exposure to infectious agents, and the like.

In certain embodiments, the treatment agents employed in the inventive methods are capable of crossing the blood brain barrier, and/or are administered using delivery systems that facilitate delivery of the agents to the central nervous system. For example, various blood brain barrier (BBB) permeability enhancers can be used, if desired, to transiently and reversibly increase the permeability of the blood brain barrier to a treatment agent. Such BBB permeability enhancers may include leukotrienes, bradykinin agonists, histamine, tight junction disruptors (e.g., zonulin, zot), hyperosmotic solutions (e.g., mannitol), cytoskeletal contracting agents, short chain alkylglycerols (e.g., 1-O-pentylglycerol), and others which are currently known in the art.

The above-mentioned and additional features of the present invention, together with the manner of obtaining them, will be best understood by reference to the following more detailed description. All references disclosed herein are hereby incorporated by reference in their entirety as if each was incorporated individually.

BRIEF DESCRIPTION OF THE DRAWINGS

FIGS. 1A, 1A1, 1B, 1B1, 1C, 1C1 and 1D show the effect of furosemide on stimulation evoked after discharge activity in rat hippocampal slices.

FIGS. 3A-3H show furosemide blockade of kainic acid-evoked electrical "status epilepticus" in urethane-anesthetized rats, with EKG recordings shown in the upper traces and cortical EEG recordings shown in the bottom traces.

DETAILED DESCRIPTION OF THE INVENTION

Figure 1C:
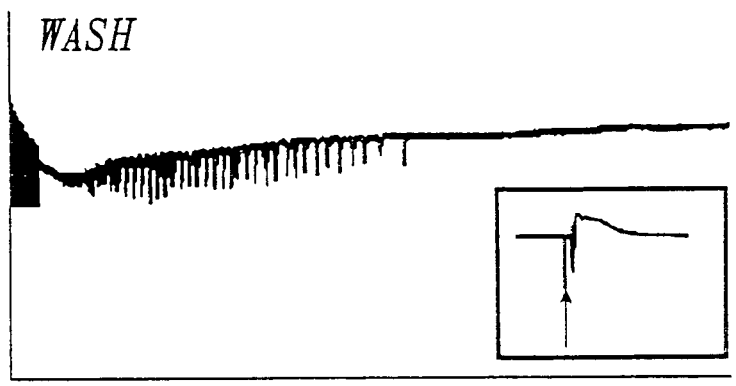

As discussed above, preferred treatment agents and methods of the present invention, for use in treating neuropathic pain and/or neuropsychiatric disorders, modulate or disrupt the synchrony of neuronal population activity in areas of heightened synchronization by reducing the activity of NKCC co-transporters. As described in detail below and illustrated in the examples, movement of ions and modulation of ionic gradients by means of ion-dependent co-transporters, preferably cation-chloride dependent co-transporters, is critical to regulation of neuronal synchronization. Chloride co-transport function has long been thought to be directed primarily to movement of chloride out of cells. The sodium independent transporter, which has been shown to be neuronally localized, moves chloride ions out of neurons. Blockade of this transporter, such as by administration of the loop diuretic furosemide, leads to hyperexcitability, which is the short-term response to cation-chloride co-transporters such as furosemide. However, the long-term response to furosemide demonstrates that the inward, sodium-dependent movement of chloride ions, mediated by the glial associated $Na^+$—$K^+$-$2Cl^-$ co-transporter NKCC1, plays an active role in blocking neuronal synchronization, without affecting excitability and stimulus-evoked cellular activity. Haglund and Hochman have demonstrated that the loop diuretic furosemide is able to block epileptic activity in humans while not affecting normal brain activity (*J. Neurophysiol.* (Feb. 23, 2005) doi:10.1152/jn.00944.2004). These results provide support for the belief that the inventive methods and compositions may be effectively employed in the treatment of neuropathic pain without giving rise to undesirable side effects often seen with conventional treatments.

As discussed above, the NKCC1 splice variant referred to as NKCC1b is more active than the NKCC1a variant. A central or peripheral nervous system which expresses a few more percentage NKCC1b may thus be more prone to disorders such as neuropathic pain and epilepsy. Similarly, a treatment agent that is more specific for NKCC1b compared to NKCC1a may be more effective in the treatment of such disorders.

The inventive methods may be used for the treatment and/or prophylaxis of neuropathic pain having, for example, the following etiologies: alcohol abuse; diabetes; eosinophilia-myalgia syndrome; Guillain-Barre syndrome; exposure to heavy metals such as arsenic, lead, mercury, and thallium; HIV/AIDS; malignant tumors; medications including amiodarone, aurothioglucose, cisplatinum, dapsone, stavudine, zalcitabine, didanosine, disulfiram, FK506, hydralazine, isoniazid, metronidazole, nitrofurantoin, paclitaxel, phenyloin and vincristine; monoclonal gammopathies; multiple sclerosis; post-stroke central pain, postherpetic neuralgia; trauma including carpal tunnel syndrome, cervical or lumbar radiculopathy, complex regional pain syndrome, spinal cord injury and stump pain; trigeminal neuralgia; vasculitis; vitamin B6 megadosing; and certain vitamin deficiencies (B12, B1, B6, E). Neuropsychiatric disorders that may be effectively treated using the inventive methods include, but are not limited to, bipolar disorders, anxiety, panic attacks, depression, schizophrenia and post-traumatic stress syndrome.

Compositions that may be effectively employed in the inventive methods are capable of reducing the effective amount, inactivating, and/or inhibiting the activity of a $Na^+$—$K^+$-$2Cl^-$ (NKCC) co-transporter. Preferably such compositions are capable of reducing the effective amount, inactivating, and/or inhibiting the activity of the co-transporter NKCC1. In certain embodiments, the inventive compositions comprise at least one treatment agent selected from the group consisting of: antagonists of NKCC1 (including but not limited to, small molecule inhibitors of NKCC1, antibodies, or antigen-binding fragments thereof, that specifically bind to NKCC1 and soluble NKCC1 ligands); anti-sense oligonucleotides to NKCC1; NKCC1-specific small interfering RNA molecules (siRNA or RNAi); and engineered soluble NKCC1 molecules. In preferred embodiments, the treatment agent is selected from the group consisting of: loop diuretics such as furosemide, bumetanide, ethacrynic acid, torsemide, azosemide, muzolimine, piretanide, tripamide and the like; thiazide and thiazide-like diuretics, such as bendroflumethiazide, benzthiazide, chlorothiazide, hydrochlorothiazide, hydro-flumethiazide, methylclothiazide, polythiazide, trichlormethiazide, chlorthalidone, indapamide, metolazone and quinethazone; and analogs and functional derivatives of such components.

Compositions of the subject invention are suitable for human and veterinary applications and are preferably delivered as pharmaceutical compositions. Pharmaceutical compositions comprise one or more treatment agents and a physiologically acceptable carrier. Pharmaceutical compositions of the present invention may also contain other compounds, which may be biologically active or inactive. For example, one or more treatment agents of the present invention may be combined with another agent, in a treatment combination, and administered according to a treatment regimen of the present invention. Such combinations may be administered as separate compositions, combined for delivery in a complementary delivery system, or formulated in a combined composition, such as a mixture or a fusion compound. Additionally, the aforementioned treatment combination may include a BBB permeability enhancer and/or a hyperosmotic agent.

While any suitable carrier known to those of ordinary skill in the art may be employed in the pharmaceutical compositions of this invention, the preferred carrier depends upon the preferred mode of administration. Compositions of the present invention may be formulated for any appropriate mode of administration, including for example, topical, oral, sublingual, nasal, inhalation (for example in either a powdered or nebulized form), rectal, intravenous (including continuous i.v. transfusion), intracranial, spinal tap, intraperitoneal, transdermal, subcutaneous or intramuscular administration. Direct intrathecal injection or administration into the cerebral spinal fluid via the spinal cord by injection, osmotic pump or other means may be employed for certain applications. The inventive compositions may also be delivered, for example injected, to or near the origin of the neuropathic pain.

For parenteral administration, such as by subcutaneous injection, the carrier preferably comprises water, saline, glycerin, propylene glycol, alcohol, a fat, a wax and/or a buffer. For oral administration, any of the above carriers, or a solid carrier such as mannitol, lactose, starch, magnesium stearate, sodium lauryl sulphate, lactose, sodium citrate, calcium carbonate, calcium phosphate, silicates, polyethylene glycol, sodium saccharine, talcum, cellulose, glucose, sucrose, dyes, and magnesium carbonate, may be employed. For rectal administration, an aqueous gel formulation, or other suitable formulations that are well known in the art may be used. Solid compositions may also be employed as fillers in soft and hard filled gelatin capsules. Preferred materials for this include lactose or mild sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

The compositions described herein may be administered as part of a sustained release formulation. Such formulations may generally be prepared using well-known technology and administered by, for example, oral, rectal or transdermal delivery systems, or by implantation of a formulation or therapeutic device at one or more desired target site(s). Sustained-release formulations may contain a treatment composition comprising an inventive treatment agent alone, or in combination with a second treatment agent, dispersed in a carrier matrix and/or contained within a reservoir surrounded by a rate controlling membrane. Carriers for use within such formulations are biocompatible, and may also be biodegradable. According to one embodiment, the sustained release formulation provides a relatively constant level of active composition release. According to another embodiment, the sustained release formulation is contained in a device that may be actuated by the subject or medical personnel, upon onset of certain symptoms, for example, to deliver predetermined dosages of the treatment composition. The amount of the treatment composition contained within a sustained release formulation depends upon the site of implantation, the rate and expected duration of release, and the nature of the condition to be treated or prevented.

In certain embodiments, compositions of the present invention for treatment of neuropathic pain and neuropsychiatric disorders are administered using a formulation and a route of administration that facilitates delivery of the treatment composition(s) to the central nervous system. Treatment compositions, such as NKCC1 antagonists, may be formulated to facilitate crossing of the blood brain barrier as described above, or may be co-administered with an agent that crosses the blood brain barrier. Treatment compositions may be delivered in liposome formulations, for example, that cross the blood brain barrier, or may be co-administered with other compounds, such as bradykinins, bradykinin analogs or derivatives, or other compounds, such as SERAPORT™, that cross the blood brain barrier. Alternatively, treatment compositions of the present invention may be delivered using a spinal tap that places the treatment composition directly in the circulating cerebrospinal fluid. For some treatment conditions, there may be transient or permanent breakdowns of the blood brain barrier and specialized formulation of the treatment composition to cross the blood brain barrier may not be necessary. We have determined, for example, that a bolus iv injection of 20 mg furosemide reduces or abolishes both spontaneous interictal activity and electrical stimulation-evoked epileptiform activity in human patients who are refractory to antiepileptic drugs (AEDs) (Haglund & Hochman *J. Neurophysiol*. (Feb. 23, 2005) doi:10.1152/jn.00944.2004).

Routes and frequency of administration of the therapeutic compositions disclosed herein, as well as dosages, vary according to the indication, and from individual to individual, and may be readily determined by a physician from information that is generally available, and by monitoring patients and adjusting the dosages and treatment regimen accordingly using standard techniques. In general, appropriate dosages and treatment regimen provide the active composition(s) in an amount sufficient to provide therapeutic and/or prophylactic benefit. Dosages and treatment regimen may be established by monitoring improved clinical outcomes in treated patients as compared to non-treated patients. A therapeutically effective dose is an amount of a compound that, when administered as described above, produces a therapeutic response in a patient. Therapeutically effective dosages and treatment regimen will depend on the condition, the severity of the condition, and the general state of the patient being treated. Since the pharmacokinetics and pharmacodynamics of the treatment compositions of the present invention vary in different patients, a preferred method for determining a therapeutically effective dosage in a patient is to gradually escalate the dosage and monitor the clinical and laboratory indicia. For combination therapy, the two or more agents are coadministered such that each of the agents is present in a therapeutically effective amount for sufficient time to produce a therapeutic or prophylactic effect. The term "coadministration" is intended to encompass simultaneous or sequential administration of two or more agents in the same formulation or unit dosage form or in separate formulations. Appropriate dosages and treatment regimen for treatment of acute episodic conditions, chronic conditions, or prophylaxis will necessarily vary to accommodate the condition of the patient.

By way of example, for the treatment to neuropathic pain, furosemide may be administered orally to a patient in amounts of 10-40 mg at a frequency of 1-3 times per day, preferably in an amount of 40 mg three times per day. In an alternative example, bumetanide may be administered orally for the treatment of neuropathic pain in amounts of 1-10 mg at a frequency of 1-3 times per day. One of skill in the art will appreciate that smaller doses may be employed, for example, in pediatric applications.

Methods and systems of the present invention may also be used to evaluate candidate compounds and treatment regimen for the treatment and/or prophylaxis of neuropathic pain and neuropsychiatric disorders. Various techniques for generating candidate compounds potentially having the desired NKCC1 cotransporter antagonist activity may be employed. Candidate compounds may be generated using procedures well known to those skilled in the art of synthetic organic chemistry. Structure-activity relationships and molecular modeling techniques are useful for the purpose of modifying known NKCC1 antagonists, such as loop diuretics, including furosemide, bumetanide, ethacrinic acid and related compounds, to confer the desired activities and specificities. Methods for screening candidate compounds for desired activities are described in U.S. Pat. Nos. 5,902,732, 5,976,825, 6,096,510 and 6,319,682, which are incorporated herein by reference in their entireties.

Candidate compounds may be screened for NKCC1 antagonist activity using screening methods of the present invention with various types of cells in culture such as glial cells, neuronal cells, renal cells, and the like, or in situ in animal models. Screening techniques to identify chloride cotransporter antagonist activity, for example, may involve altering the ionic balance of the extracellular space in the tissue culture sample, or in situ in an animal model, by producing a higher than "normal" anionic chloride concentration. The geometrical and/or optical properties of the cell or tissue sample subject to this altered ionic balance are determined, and candidate agents are administered. Following administration of the candidate agents, the corresponding geometrical and/or optical properties of the cell or tissue sample are monitored to determine whether the ionic imbalance remains, or whether the cells responded by altering the ionic balances in the extracellular and intracellular space. If the ionic imbalance remains, the candidate agent is likely a chloride cotransporter antagonist. By screening using various types of cells or tissues, candidate compounds having a high level of glial cell chloride cotransporter antagonist activity and having a reduced level of neuronal cell and renal cell chloride cotransporter antagonist activity may be identified. Similarly, effects on different types of cells and tissue systems may be assessed.

Additionally, the efficacy of candidate compounds may be assessed by simulating or inducing a condition, such as neuropathic pain, in situ in an animal model, monitoring the geometrical and/or optical properties of the cell or tissue sample during stimulation of the condition, administering the candidate compound, then monitoring the geometrical and/or optical properties of the cell or tissue sample following administration of the candidate compound, and comparing the geometrical and/or optical properties of the cell or tissue sample to determine the effect of the candidate compound. Testing the efficacy of treatment compositions for relief of neuropathic pain can be carried using well known methods and animal models, such as that described in Bennett, *Hosp. Pract*. (Off Ed). 33:95-98, 1998.

As discussed above, compositions for use in the inventive methods may comprise a treatment agent selected from the group consisting of: antibodies, or antigen-binding fragments thereof, that specifically bind to NKCC1; soluble ligands that bind to NKCC1; anti-sense oligonucleotides to NKCC1; and small interfering RNA molecules (siRNA or RNAi) that are specific for NKCC1.

Antibodies that specifically bind to NKCC1 are known in the art and include those available from Alpha Diagnostic International, Inc. (San Antonio, Tex. 78238). An "antigen-binding site," or "antigen-binding fragment" of an antibody refers to the part of the antibody that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

A number of molecules are known in the art that comprise antigen-binding sites capable of exhibiting the binding properties of an antibody molecule. For example, the proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment, which comprises both antigen-binding sites. An "Fv" fragment can be produced by preferential proteolytic cleavage of an IgM, IgG or IgA immunoglobulin molecule, but are more commonly derived using recombinant techniques known in the art. The Fv fragment includes a non-covalent $V_H$::$V_L$ heterodimer including an antigen-binding site which retains much of the antigen recognition and binding capabilities of the native antibody molecule (Inbar et al. *Proc. Natl. Acad. Sci. USA* 69:2659-2662, 1972; Hochman et al. *Biochem* 15:2706-2710, 1976; and Ehrlich et al. *Biochem* 19:4091-4096, 1980).

Humanized antibodies that specifically bind to NKCC1 may also be employed in the inventive methods. A number of humanized antibody molecules comprising an antigen-binding site derived from a non-human immunoglobulin have been described, including chimeric antibodies having rodent V regions and their associated CDRs fused to human constant domains (Winter et al. *Nature* 349:293-299, 1991; Lobuglio et al. *Proc. Natl. Acad. Sci. USA* 86:4220-4224, 1989; Shaw et al. *J Immunol.* 138:4534-4538, 1987; and Brown et al. *Cancer Res.* 47:3577-3583, 1987); rodent CDRs grafted into a human supporting FR prior to fusion with an appropriate human antibody constant domain (Riechmann et al. *Nature* 332:323-327, 1988; Verhoeyen et al. *Science* 239:1534-1536, 1988; and Jones et al. *Nature* 321:522-525, 1986); and rodent CDRs supported by recombinantly veneered rodent FRs (European Patent Publication No. 519,596, published Dec. 23, 1992). These "humanized" molecules are designed to minimize unwanted immunological responses towards rodent antihuman antibody molecules which limit the duration and effectiveness of therapeutic applications of those moieties in human recipients.

Modulating the activity of NKCC1 may alternatively be accomplished by reducing or inhibiting expression of the polypeptide, which can be achieved by interfering with transcription and/or translation of the corresponding polynucleotide. Polypeptide expression may be inhibited, for example, by introducing anti-sense expression vectors, anti-sense oligodeoxyribonucleotides, anti-sense phosphorothioate oligodeoxy-ribonucleotides, anti-sense oligoribonucleotides or anti-sense phosphorothioate oligoribonucleotides; or by other means well known in the art. All such anti-sense polynucleotides are referred to collectively herein as "anti-sense oligonucleotides".

The anti-sense oligonucleotides for use in the inventive methods are sufficiently complementary to the NKCC1 polynucleotide to bind specifically to the polynucleotide. The sequence of an anti-sense oligonucleotide need not be 100% complementary to the of the polynucleotide in order for the anti-sense oligonucleotide to be effective in the inventive methods. Rather an anti-sense oligonucleotide is sufficiently complementary when binding of the anti-sense oligonucleotide to the polynucleotide interferes with the normal function of the polynucleotide to cause a loss of utility, and when non-specific binding of the oligonucleotide to other, non-target sequences is avoided. The design of appropriate anti-sense oligonucleotides is well known in the art. Oligonucleotides that are complementary to the 5' end of the message, for example the 5' untranslated sequence up to and including the AUG initiation codon, should work most efficiently at inhibiting translation. However, oligonucleotides complementary to either the 5'- or 3'-non-translated, non-coding, regions of the targeted polynucleotide may also be employed. Cell permeation and activity of anti-sense oligonucleotides can be enhanced by appropriate chemical modifications, such as the use of phenoxazine-substituted C-5 propynyl uracil oligonucleotides (Flanagan et al., *Nat. Biotechnol.* 17:48-52, 1999) or 2'-O-(2-methoxy) ethyl (2'-MOE)-oligonucleotides (Zhang et al., *Nat. Biotechnol.* 18:862-867, 2000). The use of techniques involving anti-sense oligonucleotides is well known in the art and is described, for example, in Robinson-Benion et al. (*Methods in Enzymol.* 254:363-375, 1995) and Kawasaki et al. (*Artific. Organs* 20:836-848, 1996).

Expression of the NKCC1 polypeptide may also be specifically suppressed by methods such as RNA interference (RNAi). A review of this technique is found in *Science*, 288:1370-1372, 2000. Briefly, traditional methods of gene suppression, employing anti-sense RNA or DNA, operate by binding to the reverse sequence of a gene of interest such that binding interferes with subsequent cellular processes and therefore blocks synthesis of the corresponding protein. RNAi also operates on a post-translational level and is sequence specific, but suppresses gene expression far more efficiently. Exemplary methods for controlling or modifying gene expression are provided in WO 99/49029, WO 99/53050 and WO01/75164, the disclosures of which are hereby incorporated by reference. In these methods, post-transcriptional gene silencing is brought about by a sequence-specific RNA degradation process which results in the rapid degradation of transcripts of sequence-related genes. Studies have shown that double-stranded RNA may act as a mediator of sequence-specific gene silencing (see, for example, Montgomery and Fire, *Trends in Genetics*, 14:255-258, 1998). Gene constructs that produce transcripts with self-complementary regions are particularly efficient at gene silencing.

It has been demonstrated that one or more ribonucleases specifically bind to and cleave double-stranded RNA into short fragments. The ribonuclease(s) remains associated with these fragments, which in turn specifically bind to complementary mRNA, i.e. specifically bind to the transcribed mRNA strand for the gene of interest. The mRNA for the gene is also degraded by the ribonuclease(s) into short fragments, thereby obviating translation and expression of the gene. Additionally, an RNA-polymerase may act to facilitate the synthesis of numerous copies of the short fragments, which exponentially increases the efficiency of the system. A unique feature of RNAi is that silencing is not limited to the cells where it is initiated. The gene-silencing effects may be disseminated to other parts of an organism.

The NKCC1 polynucleotide may thus be employed to generate gene silencing constructs and/or gene-specific self-complementary, double-stranded RNA sequences that can be employed in the inventive methods using delivery methods known in the art. A gene construct may be employed to express the self-complementary RNA sequences. Alternatively, cells may be contacted with gene-specific double-stranded RNA molecules, such that the RNA molecules are internalized into the cell cytoplasm to exert a gene silencing effect. The double-stranded RNA must have sufficient homology to the NKCC1 gene to mediate RNAi without affecting expression of non-target genes. The double-stranded DNA is at least 20 nucleotides in length, and is preferably 21-23 nucleotides in length. Preferably, the double-stranded RNA corresponds specifically to a polynucleotide of the present invention. The use of small interfering RNA (siRNA) molecules of 21-23 nucleotides in length to suppress gene expression in mammalian cells is described in WO 01/75164. Tools for designing optimal inhibitory siRNAs include that available from DNAengine Inc. (Seattle, Wash.).

One RNAi technique employs genetic constructs within which sense and anti-sense sequences are placed in regions flanking an intron sequence in proper splicing orientation with donor and acceptor splicing sites. Alternatively, spacer sequences of various lengths may be employed to separate self-complementary regions of sequence in the construct. During processing of the gene construct transcript, intron sequences are spliced-out, allowing sense and anti-sense sequences, as well as splice junction sequences, to bind forming double-stranded RNA. Select ribonucleases then bind to and cleave the double-stranded RNA, thereby initiating the cascade of events leading to degradation of specific mRNA gene sequences, and silencing specific genes.

For in vivo uses, a genetic construct, anti-sense oligonucleotide or RNA molecule may be administered by various art-recognized procedures (see, e.g., Rolland, *Crit. Rev. Therap. Drug Carrier Systems* 15:143-198, 1998, and cited references). Both viral and non-viral delivery methods have been used for gene therapy. Useful viral vectors include, for example, adenovirus, adeno-associated virus (AAV), retrovirus, vaccinia virus and avian poxvirus. Improvements have been made in the efficiency of targeting genes to tumor cells with adenoviral vectors, for example, by coupling adenovirus to DNA-polylysine complexes and by strategies that exploit receptor-mediated endocytosis for selective targeting (see, e.g., Curiel et al., *Hum. Gene Ther.,* 3:147-154, 1992; and Cristiano & Curiel, *Cancer Gene Ther.* 3:49-57, 1996). Non-viral methods for delivering polynucleotides are reviewed in Chang & Seymour, (Eds) *Curr. Opin. Mol. Ther., vol.* 2, 2000. These methods include contacting cells with naked DNA, cationic liposomes, or polyplexes of polynucleotides with cationic polymers and dendrimers for systemic administration (Chang & Seymour, Ibid.). Liposomes can be modified by incorporation of ligands that recognize cell-surface receptors and allow targeting to specific receptors for uptake by receptor-mediated endocytosis (see, for example, Xu et al., *Mol. Genet. Metab.,* 64:193-197; 1998; and Xu et al., *Hum. Gene Ther.,* 10:2941-2952; 1999).

Tumor-targeting bacteria, such as Salmonella, are potentially useful for delivering genes to tumors following systemic administration (Low et al., *Nat. Biotechnol.* 17:37-41, 1999). Bacteria can be engineered ex vivo to penetrate and to deliver DNA with high efficiency into, for example, mammalian epithelial cells in vivo (see, e.g., Grillot-Courvalin et al., *Nat. Biotechnol.* 16:862-866, 1998). Degradation-stabilized oligonucleotides may be encapsulated into liposomes and delivered to patients by injection either intravenously or directly into a target site (for example, the origin of neuropathic pain). Alternatively, retroviral or adenoviral vectors, or naked DNA expressing anti-sense RNA for the inventive polypeptides, may be administered to patients. Suitable techniques for use in such methods are well known in the art.

The treatment compositions and methods of the present invention have been described, above, with respect to certain preferred embodiments. The Examples set forth below describe the results of specific experiments and are not intended to limit the invention in any fashion.

EXAMPLE 1

The Effects of Furosemide on Epileptiform Discharges in Hippocampal Slices

During these studies, spontaneous epileptiform activity was elicited by a variety of treatments. Sprague-Dawley rats (males and females; 25-35 days old) were decapitated, the top of the skull was rapidly removed, and the brain chilled with ice-cold oxygenated slicing medium. The slicing medium was a sucrose-based artificial cerebrospinal fluid (sACSF) consisting of 220 mM sucrose, 3 mM KCl, 1.25 mM $NaH_2PO_4$, 2 mM $MgSO_4$, 26 mM $NaHCO_3$, 2 mM $CaCl_2$, and 10 mM dextrose (295-305 mOsm). A hemisphere of brain containing hippocampus was blocked and glued (cyanoacrylic adhesive) to the stage of a Vibroslicer (Frederick Haer, Brunsick, Me.). Horizontal or transverse slices 400 μm thick were cut in 4° C., oxygenated (95% $O_2$; 5% $CO_2$) slicing medium. The slices were immediately transferred to a holding chamber where they remained submerged in oxygenated bathing medium (ACSF) consisting of 124 mM NaCl, 3 mM KCl, 1.25 mM $NaH_2PO_4$, 2 mM $MgSO_4$, 26 mM $NaHCO_3$, 2 mM $CaCl_2$, and 10 mM dextrose (295-305 mOsm). The slices were held at room temperature for at least 45 minutes before being transferred to a submersion-style recording chamber (all other experiments). In the recording chamber, the slices were perfused with oxygenated recording medium at 34-35° C. All animal procedures were conducted in accordance with NIH and University of Washington animal care guidelines.

In most slice experiments, simultaneous extracellular field electrode recordings were obtained from CA1 and CA3 areas. A bipolar tungsten stimulating electrode was placed on the Schaffer collaterals to evoke synaptically-driven field responses in CA1. Stimuli consisted of 100-300 μsec duration pulses at an intensity of four times the population-spike threshold. After discharges were evoked by a 2 second train of such stimuli delivered at 60 Hz. Spontaneous interictal-like bursts were observed in slices treated by the following modifications or additions to the bathing medium: 10 mM potassium (6 slices; 4 animals; average—81 bursts/min.); 200-300 μM 4-aminopyridine (4 slices; 2 animals; average—33 burst/min.); 50-100 μM bicuculline (4 slices; 3 animals; average—14 bursts/min); M $Mg^{++}$ (1 hour of perfusion—3 slices; 2 animals; average—20 bursts/min. or 3 hours of perfusion—2 slices; 2 animals); zero calcium/6 mM KCl and 2 mM EGTA (4 slices; 3 animals). In all treatments, furosemide was added to the recording medium once a consistent level of bursting was established.

In the first of these procedures, episodes of after discharges were evoked by electrical stimulation of the Schaffer collaterals (Stasheff et al., *Brain Res.* 344:296, 1985) and the extracellular field response was monitored in the CA1 pyramidal cell region (13 slices; 8 animals). The concentration of $Mg^{++}$ in the bathing medium was reduced to 0.9 mM and after discharges were evoked by stimulation at 60 Hz for 2 seconds at an intensity 4 times the population spike threshold (population spike threshold intensity varied between 20-150 μA at 100-300 μsec pulse duration). The tissue was allowed to recover for 10 minutes between stimulation trials. In each experiment, the initial response of CA1 to synaptic input was first tested by recording the field potential evoked by a single stimulus pulse. In the control condition, Schaffer collateral stimulation evoked a single population spike (FIG. 1A, inset). Tetanic stimulation evoked approximately 30 seconds after discharge (FIG. 1A, left) associated with a large change in intrinsic signal (FIG. 1A, right).

For imaging of intrinsic optical signals, the tissue was placed in a perfusion chamber located on the stage of an upright microscope and illuminated with a beam of white light (tungsten filament light and lens system; Dedo Inc.) directed through the microscope condenser. The light was controlled and regulated (power supply—Lamda Inc.) to minimize fluctuations and filtered (695 nm longpass) so that the slice was transilluminated with long wavelengths (red).

Field of view and magnification were determined by the choice of microscope objectives (4× for monitoring the entire slice). Image-frames were acquired with a charge-coupled device (CCD) camera (Dage MTI Inc.) at 30 HZ and were digitized at 8 bits with a spatial resolution of 512×480 pixels using an Imaging Technology Inc. Series 151 imaging system; gains and offsets of the camera-control box and the A/D board were adjusted to optimize the sensitivity of the system. Imaging hardware was controlled by a 486-PC compatible computer. To increase signal/noise, an averaged-image was composed from 16 individual image-frames, integrated over 0.5 sec and averaged together. An experimental series typically involved the continuous acquisition of a series of averaged-images over a several minute time period; at least 10 of these averaged-images were acquired as control-images prior o stimulation. Pseudocolored images were calculated by subtracting the first control-image from subsequently acquired images and assigning a color lookup table to the pixel values. For these images, usually a linear low-pass filter was used to remove high frequency noise and a linear-histogram stretch was used to map the pixel values over the dynamic range of the system. All operations on these images were linear so that quantitative information was preserved. Noise was defined as the maximum standard deviation of fluctuations of $\Delta R/R$ of the sequence of control images within a given acquisition series, where $\Delta R/R$ represented the magnitude of the change in light-transmission through the tissue. Delta R/R was calculated by taking all the difference-images and dividing by the first control image: (subsequent image—first-control-image)/first-control-image. The noise was always <0.01 for each of the chosen image sequences. The absolute change in light transmission through the tissue was estimated during some experiments by acquiring images after placing neutral density filters between the camera and the light source. On average, the camera electronics and imaging system electronics amplified the signal 10-fold prior to digitization so that the peak absolute changes in light transmission through the tissue were usually between 1% and 2%.

Figure 1D:
Figure 1D:

The gray-scale photo shown in FIG. 1D is a video image of a typical hippocampal slice in the recording chamber. The fine gold-wire mesh that was used to hold the tissue in place can be seen as dark lines running diagonally across the slice. A stimulating electrode can be seen in the upper right on the stratum radiatum of CA1. The recording electrode (too thin to be seen in the photo) was inserted at the point indicated by the white arrow. FIG. 1A illustrates that two seconds of stimulation at 60 Hz elicited after discharge activity and shows a typical after discharge episode recorded by the extracellular electrode. The inset of FIG. 1A shows the CA1 field response to a single 200 sec test pulse (artifact at arrow) delivered to the Schaffer collaterals. FIG. 1A1 shows a map of the peak change in optical transmission through the tissue evoked by Schaffer collateral stimulation. The region of maximum optical change corresponds to the apical and basal dendritic regions of CA1 on either side of the stimulating electrode. FIG. 1B illustrates sample traces showing responses to stimulation after 20 minutes of perfusion with medium containing 2.5 mM furosemide. Both the electrical after discharge activity (shown in FIG. 1B) and the stimulation-evoked optical changes (shown in FIG. 1B1) were blocked. However, there was a hyper-excitable field response (multiple population spikes) to the test pulse (inset). FIGS. 1C and 1C1 illustrate that restoration of initial response patterns was seen after 45 minutes of perfusion with normal bathing medium.

The opposing effects of furosemide-blockade of the stimulation-evoked after discharges and a concomitant increase of the synaptic response to a test-pulse illustrate the two key results: (1) furosemide blocked epileptiform activity, and (2) synchronization (as reflected by spontaneous epileptiform activity) and excitability (as reflected by the response to a single synaptic input) were dissociated. Experiments in which the dose-dependency of furosemide was examined determined that a minimum concentration of 1.25 mM was required to block both the after discharges and optical changes.

EXAMPLE 2

Figure 2A:
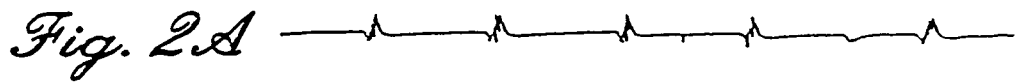
FIGS. 2A-2R show furosemide blockade of spontaneous epileptiform burst discharges across a spectrum of in vitro models.
Figure 2B:
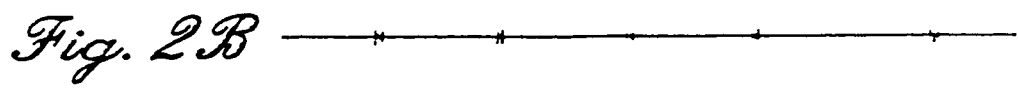
Figure 2C:
Figure 2D:
Figure 2E:
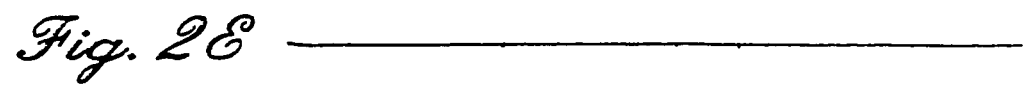
Figure 2F:
Figure 2G:
Figure 2H:
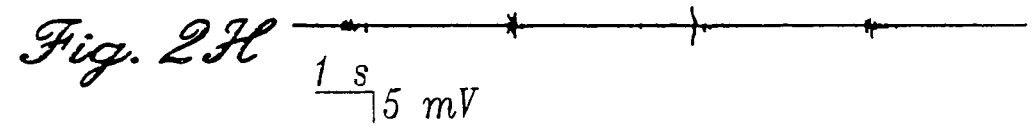

The Effects of Furosemide on Epileptiform Discharges in Hippocampal Slices Perfused with High-$K^+$ (10 mM) Bathing Medium Rat hippocampal slices, prepared as described above, were perfused with a high-$K^+$ solution until extended periods of spontaneous interictal-like bursting were recorded simultaneously in CA3 (top traces) and CA1 (lower traces) pyramidal cell regions (FIGS. 2A and 2B). After 15 minutes of perfusion with furosemide-containing medium (2.5 mM furosemide), the burst discharges increased in magnitude (FIGS. 2C and 2D). However, after 45 minutes of furosemide perfusion, the bursts were blocked in a reversible manner (FIGS. 2E, 2F, 2G and 2H). During this entire sequence of furosemide perfusion, the synaptic response to a single test pulse delivered to the Schaffer colalterals was either unchanged or enhanced (data not shown). It is possible that the initial increase in discharge amplitude reflected a furosemide-induced decrease in inhibition (Misgeld et al., *Science* 232:1413, 1986; Thompson et al., *J. Neurophysiol.* 60:105, 1988; Thompson and Gähwiler, *J. Neuropysiol.* 61:512, 1989; and Pearce, *Neuron* 10:189, 1993). It has previously been reported (Pearce, *Neuron* 10:189, 1993) that furosemide blocks a component of the inhibitory currents in hippocampal slices with a latency (<15 min.) similar to the time to onset of the increased excitability observed here. The longer latency required for the furosemide-block of the spontaneous bursting might correspond to additional time required for a sufficient block of the furosemide-sensitive cellular volume regulation mechanisms under high-$K^+$ conditions.

Figure 2I:
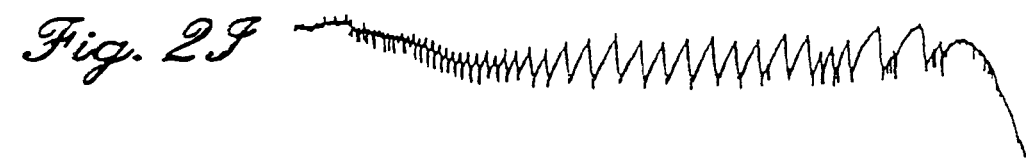
Figure 2J:
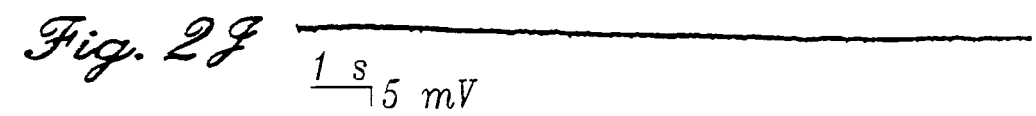
Figure 2K:
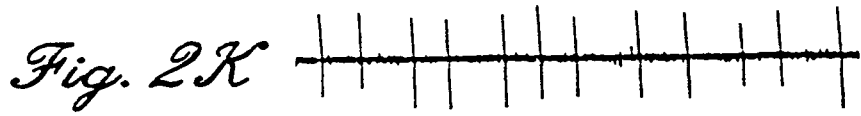
Figure 2L:
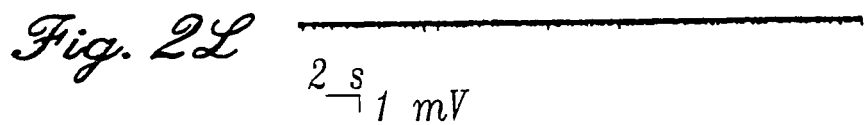
Figure 2M:
Figure 2N:
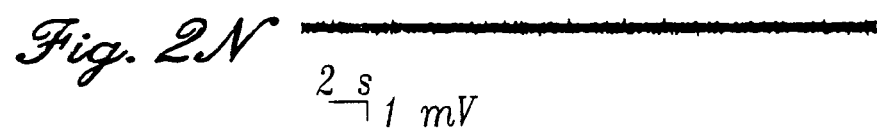
Figure 2O:
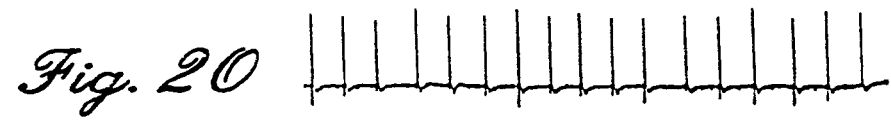
Figure 2P:
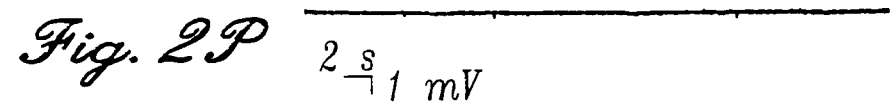
Figure 2Q:
Figure 2R:
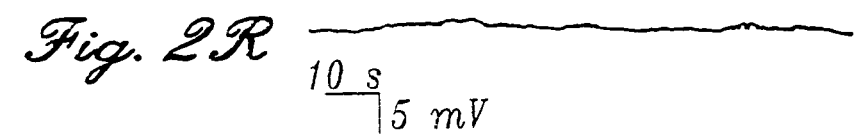

After testing the effects of furosemide on slices perfused with high-$K^+$, similar studies were performed with a variety of other commonly studied in vitro models of epileptiform discharge (Galvan et al., *Brain Res.* 241:75, 1982; Schwartzkroin and Prince, *Brain Res.* 183:61, 1980; Anderson et al., *Brain Res.* 398:215, 1986; and Zhang et al., *Epilepsy Res.* 20:105, 1995). After prolonged exposure (2-3 hours) to magnesium-free medium (O—$Mg^{++}$), slices have been shown to develop epileptiform discharges that are resistant to common clinically used anticonvulsant drugs (Zhang et al., *Epilepsy Res.* 20:105, 1995). Recordings from entorhinal cortex (FIG. 2I) and subiculum (not shown) showed that after 3 hours of perfusion with O—$Mg^{++}$ medium, slices developed bursting patterns that appeared similar to these previously described "anticonvulsant resistant" bursts. One hour after the addition of furosemide to the bathing medium, these bursts were blocked (FIG. 2J). Furosemide also blocked spontaneous burst discharges observed with the following additions/modifications to the bathing medium: (1) addition of 200-300 μM 4-aminopyridine (4-AP; a potassium channel blocker) (FIGS. 2K and 2L); (2) addition of the GABA antagonist, bicuculline, at 50-100 μM (FIGS. 2M and 2N); (3) removal of magnesium (O—$Mg^{++}$)-1 hours perfusion (FIGS. 2O and 2P); and (4) removal of calcium plus extracellular chelation (O—$Ca^{++}$) (FIGS. 2Q and 2R). With each of these manipulations, spontaneous interictal-like patterns were simultaneously recorded from CA1 and CA3 subfields (FIGS. 2K, 2L, 2M and 2N show only the CA3 trace and FIGS. 2O, 2P, 2Q, and 2R show only the CA1 trace). In the O—$Ca^{++}$ experiments, 5 mM furosemide blocked the bursting with a latency of 15-20 minutes. For all other protocols, bursting was blocked by 2.5 mM furosemide with a latency of 20-60 minutes. Furosemide reversibly blocked the spontaneous bursting activity in both CA1 and CA3 in all experiments (FIGS. 2L, 2N, 2P and 2R).

EXAMPLE 3

The Effects of Furosemide on Epileptiform Activity Induced by i.v. Injection of Kainic Acid in Anesthetized Rats This example illustrates an in vitro model in which epileptiform activity was induced by i.v. injection of kainic acid (KA) into anesthetized rats (Lothman et al., *Neurology* 31:806, 1981). The results are illustrated in FIGS. 3A-3H. Sprague-Dawley rats (4 animals; weights 250-270 g) were anesthetized with urethane (1.25 g/kg i.p.) and anesthesia maintained by additional urethane injections (0.25 g/kg i.p.) as needed. Body temperature was monitored using a rectal temperature probe and maintained at 35-37° C. with a heating pad; heart rate (EKG) was continuously monitored. The jugular vein was cannulated on one side for intravenous drug administration. Rats were placed in a Kopf stereotaxic device (with the top of the skull level), and a bipolar stainless-steel microelectrode insulated to 0.5 mm of the tip was inserted to a depth of 0.5-1.2 mm from the cortical surface to record electroencephalographic (EEG) activity in the fronto-parietal cortex. In some experiments, a 2M NaCl-containing pipette was lowered to a depth of 2.5-3.0 mm to record hippocampal EEG. Data were stored on VHS videotape and analyzed off-line.

Following the surgical preparation and electrode placement, animals were allowed to recover for 30 minutes before the experiments were initiated with an injection of kainic acid (10-12 mg/kg i.v.). Intense seizure activity, an increased heart rate, and rapid movements of the vibrissae were induced with a latency of about 30 minutes. Once stable electrical seizure was evident, furosemide was delivered in 20 mg/kg boluses every 30 minutes to a total of 3 injections. Experiments were terminated with the intravenous administration of urethane. Animal care was in accordance with NIH guidelines and approved by the University of Washington Animal Care Committee.

FIGS. 3A-3H show furosemide blockade of kainic acid-evoked electrical "status epilepticus" in urethane-anesthetized rats. EKG recordings are shown as the top traces and EEG recordings are shown as the bottom traces. In this model, intense electrical discharge (electrical "status epilepticus") was recorded from the cortex (or from depth hippocampal electrodes) 30-60 minutes after KA injection (10-12 mg/kg) (FIGS. 3C and 3D). Control experiments (and previous reports, Lothman et al., *Neurology*, 31:806, 1981) showed that this status-like activity was maintained for well over 3 hours. Subsequent intravenous injections of furosemide (cumulative dose: 40-60 mg/kg) blocked seizure activity with a latency of 30-45 minutes, often producing a relatively flat EEG (FIGS. 3E, 3F, 3G and 3H). Even 90 minutes after the furosemide injection, cortical activity remained near normal baseline levels (i.e., that observed prior to the KA and furosemide injections). Studies on the pharmacokinetics of furosemide in the rat indicate that the dosages used in this example were well below toxic levels (Hammarlund and Paalzow, *Biopharmaceutics Drug Disposition*, 3:345, 1982).

Experimental Methods for Examples 4-7

Hippocampal slices were prepared from Sprague-Dawley adult rats as described previously. Transverse hippocampal slices 100 µm thick were cut with a vibrating cutter. Slices typically contained the entire hippocampus and subiculum. After cutting, slices were stored in an oxygenated holding chamber at room temperature for at least one hour before recording. All recordings were acquired in an interface type chamber with oxygenated (95% $O_2$, 5% $CO_2$) artificial cerebral spinal fluid (ACSF) at 34°-35° C. Normal ACSF contained (in mmol/l): 124 NaCl, 3 KCl, 1.25 $NaH_2PO_4$, 1.2 $MgSO_4$, 26 $NaHCO_3$, 2 $CaCl_2$, and 10 dextrose.

Sharp-electrodes for intracellular recordings from CA1 and CA3 pyramidal cells were filled with 4 M potassium acetate. Field recordings from the CA1 and CA3 cell body layers were acquired with low-resistance glass electrodes filled with 2 M NaCl. For stimulation of the Schaffer collateral or hilar pathways, a small monopolar tungsten electrode was placed on the surface of the slice. Spontaneous and stimulation-evoked activities from field and intracellular recordings were digitized (Neurocorder, Neurodata Instruments, New York, N.Y.) and stored on videotape. AxoScope software (Axon Instruments) on a personal computer was used for off-line analysis of data.

In some experiments, normal or low-chloride medium was used containing bicuculline (20 µM), 4-amino pyridine (4-AP) (100 µM), or high-$K^+$ (7.5 or 12 mM). In all experiments, low-chloride solutions (7, and 21 mM $[Cl^-]_o$) were prepared by equimolar replacement of NaCl with $Na^+$-gluconate (Sigma). All solutions were prepared so that they had a pH of approximately 7.4 and an osmolarity of 290-300 mOsm at 35° C. and at equilibrium from carboxygenation with 95% $O_2$/5% $CO_2$.

After placement in the interface chamber, slices were superfused at approximately 1 ml/min. At this flow-rate, it took 8-10 minutes for changes in the perfusion media to be completed. All of the times reported here have taken this delay into account and have an error of approximately ±2 minutes.

EXAMPLE 4

Timing of Cessation of Spontaneous Epileptiform Bursting in Areas in CA1 and CA3

The relative contributions of the factors that modulate synchronized activity vary between areas CA1 and CA3. These factors include differences in the local circuitry and region-specific differences in cell packing and volume fraction of the extracellular spaces. If the anti-epileptic effects of anion or chloride-cotransport antagonism are due to a desynchronization in the timing of neuronal discharge, chloride-cotransport blockade might be expected to differentially affect areas CA1 and CA3. To test this, a series of experiments was performed to characterize differences in the timing of the blockade of spontaneous epileptiform activity in areas CA1 and CA3.

Field activity was recorded simultaneously in areas CA1 and CA3 (approximately midway between the most proximal and distal extent the CA3 region), and spontaneous bursting was induced by treatment with high-$[K^+]_o$ (12 µM; n=12), bicuculline (20 mM; n=12), or 4-AP (100 µM; n=5). Single electrical stimuli were delivered to the Schaffer collaterals, midway between areas CA1 and CA3, every 30 seconds so that the field responses in areas CA1 and CA3 could be monitored throughout the duration of each experiment. In all experiments, at least 20 minutes of continuous spontaneous epileptiform bursting was observed prior to switching to low $[Cl^-]_o$ (21 mM) or furosemide-containing (2.5 mM) medium.

In all cases, after 30-40 minutes exposure to furosemide or low-chloride medium, spontaneous bursting ceased in area CA1 before the bursting ceased in area CA3. The temporal sequence of events typically observed included an initial increase in burst frequency and amplitude of the spontaneous field events, then a reduction in the amplitude of the burst discharges which was more rapid in CA1 than in CA3. After CA1 became silent, CA3 continued to discharge for 5-10 minutes, until it too no longer exhibited spontaneous epileptiform events.

This temporal pattern of burst cessation was observed with all epileptiform-inducing treatments tested, regardless of whether the agent used for blockade of spontaneous bursting was furosemide or low-$[Cl^-]_o$ medium. Throughout all stages of these experiments, stimulation of the Schaffer collaterals evoked hyperexcited field responses in both the CA1 and CA3 cell body layers. Immediately after spontaneous bursting was blocked in both areas CA1 and CA3, hyperexcited population spikes could still be evoked.

We considered the possibility that the observed cessation of bursting in CA1 prior to CA3 was an artifact of the organization of synaptic contacts between these areas relative to our choice of recording sites. It is known that the projections of the various subregions of CA3 terminate in an organized fashion in CA1; CA3 cells closer to the dentate gyrus (proximal CA3) tend to project most heavily to the distal portions of CA1 (near the subicular border), whereas CA3 projections arising from cells located more distally in CA3 terminate more heavily in portions of CA1 located closer to the CA2 border. If the cessation of bursting occurs in the different subregions of CA3 at different times, the results of the above set of experiments might arise not as a difference between CA1 and CA3, but rather as a function of variability in bursting activity across CA3 subregions. We tested this possibility in three experiments. Immediately after the spontaneous bursting ceased in CA1, we surveyed the CA3 field with a recording electrode. Recordings from several different CA3 locations (from the most proximal to the most distal portions of CA3), showed that all subregions of area CA3 were spontaneously bursting during the time that CA1 was silent.

The observation that CA3 continued to discharge spontaneously after CA1 became silent was unexpected since population discharges in CA3 are generally thought to evoke discharges in CA1 through excitatory synaptic transmission. As previously described, single-pulse stimuli delivered to the Schaffer collaterals still evoked multiple population spikes in CA1 even after the blockade of spontaneous bursting; thus, hyperexcited excitatory synaptic transmissions in CA3-to-CA1 synapse was intact. Given this maintained efficacy of synaptic transmission, and the continued spontaneous field discharges in CA3, we postulated that the loss of spontaneous bursting in CA1 was due to a decrease in synchronization of incoming excitatory drive. Further, since spontaneous epileptiform discharge in CA3 also eventually ceased, perhaps this desynchronization process occurred at different times in the two hippocampal subfields.

EXAMPLE 5

Effect of Chloride-Cotransport Antagonism on the Synchronization of CA1 and CA3 Field Population Discharges The observation from Example 4 suggested a temporal relationship between the exposure time to low-$[Cl^-]_o$ or furosemide-containing medium and the characteristics of the spontaneous burst activity. Further, this relationship was different between areas CA1 and CA3. In order to better characterize the temporal relationships, we compared the occurrences of CA1 action potentials and the population spike events in the field responses of CA1 and CA3 subfields during spontaneous and stimulation-evoked burst discharge.

Intracellular recordings were obtained from CA1 pyramidal cells, with the intracellular electrode placed close (<100 μM) to the CA1 field electrode. The slice was stimulated every 20 seconds with single stimuli delivered to the Schaffer collaterals. After continuous spontaneous bursting was established for at least 20 minutes, the bathing medium was switched to bicuculline-containing low-$[Cl^-]_o$ (21 mM) medium. After approximately 20 minutes, the burst frequency and amplitude was at its greatest. Simultaneous field and intracellular recordings during this time showed that the CA1 field and intracellular recordings were closely synchronized with the CA3 field discharges. During each spontaneous discharge, the CA3 field response preceded the CA1 discharge by several milliseconds. During stimulation-evoked events, action potential discharges of the CA1 pyramidal cell were closely synchronized to both CA3 and CA1 field discharges.

With continued exposure to low-$[Cl^-]_o$ medium, the latency between the spontaneous discharges of areas CA1 and CA3 increased, with a maximum latency of 30-40 milliseconds occurring after 30-40 minutes exposure to the bicuculline-containing low-chloride medium. During this time, the amplitude of both the CA1 and CA3 spontaneous field discharges decreased. Stimulation-evoked discharges during this time closely mimicked the spontaneously occurring discharges in morphology and relative latency. However, the initial stimulus-evoked depolarization of the neuron (presumably, the monosynaptic EPSP) began without any significant increase in latency. The time interval during which these data were acquired corresponds to the time immediately prior to the cessation of spontaneous bursting in CA1.

After 40-50 minutes perfusion with low-$[Cl^-]_o$ medium, the spontaneous bursts were nearly abolished in CA1 but were unaffected in CA3. Schaffer collateral stimulation during this time showed that monosynaptically-triggered responses of CA1 pyramidal cells occurred without any significant increase in latency, but that stimulation-evoked field responses were almost abolished. The time interval during which these data were acquired corresponds to the moments immediately prior to the cessation of spontaneous bursting in CA3.

After prolonged exposure to low-$[Cl^-]_o$ medium, large increases (>30 milliseconds) developed in the latency between Schaffer collateral stimulation and the consequent CA3 field discharge. Eventually, no field responses could be evoked by Schaffer collateral stimulation in either areas CA1 and CA3. However, action potential discharge from CA1 pyramidal cells in response to Schaffer collateral stimulation could be evoked with little change in response latency. Indeed, for the entire duration of the experiments (greater than two hours), action potential discharges form CA1 pyramidal cells could be evoked at short latency by Schaffer collateral stimulation. Further, although stimulation-evoked hyperexcited discharges of CA3 were eventually blocked after prolonged exposure to low-$[Cl^-]_o$ medium, the antidromic response in CA3 appeared to be preserved.

EXAMPLE 6

Effects of Chloride-Cotransport Antagonism on the Synchronization of Burst Discharges in CA1 Pyramidal Cells The foregoing data suggest the disappearance of the field responses may be due to a desynchronization of the occurrence of action potentials among neurons. That is, although synaptically-driven excitation of CA1 pyramidal cells was not preserved, action potential synchrony among the CA1 neuronal population was not sufficient to summate into a measurable DC field response. In order to test this, paired intracellular recordings of CA1 pyramidal cells were acquired simultaneously with CA1 field responses. In these experiments, both the intracellular electrodes and the field recording electrodes were placed within 200 µm of one another.

During the period of maximum spontaneous activity induced by bicuculline-containing low-$[Cl^-]_o$ medium, recordings showed that action potentials between pairs of CA1 neurons and the CA1 field discharges were tightly synchronized both during spontaneous and stimulation-evoked discharges. After continued exposure to low-$[Cl^-]_o$ medium, when the amplitude of the CA1 field discharge began to broaden and diminish, both spontaneous and stimulation-evoked discharges showed a desynchronization in the timing of the occurrences of action potentials between pairs of CA1 neurons, and between the action potentials and the field responses. This desynchronization was coincident with the suppression of CA1 field amplitude. By the time that spontaneous bursting in CA1 ceased, a significant increase in latency had developed between Schaffer collateral stimulation and CA1 field discharge. At this time, paired intracellular recordings showed a dramatic desynchronization in the timing of action potential discharge between pairs of neurons and between the occurrence of action potentials and the field discharges evoked by Schaffer collateral stimulation.

It is possible that the observed desynchronization of CA1 action potential discharge is due to the randomization of mechanisms necessary for synaptically-driven action potential generation, such as a disruption in the timing of synaptic release or random conduction failures at neuronal processes. If this were the case, then one would expect that the occurrence of action potentials between a given pair of neurons would vary randomly with respect to one another, from stimulation to stimulation. We tested this by comparing the patterns of action potential discharge of pairs of neurons between multiple consecutive stimuli of the Schaffer collaterals. During each stimulation event, the action potentials occurred at nearly identical times with respect to one another, and showed an almost identical burst morphology from stimulation to stimulation. We also checked to see whether the occurrence of action potentials between a given pair of neurons during spontaneous field discharges was fixed in time. The patterns of action potential discharges from a given pair of CA1 neurons was compared between consecutive spontaneous field bursts during the time when the occurrence of action potentials was clearly desynchronized. Just as in the case of stimulation-evoked action potential discharge described above, the action potentials generated during a spontaneous population discharge occurred at nearly identical times with respect to one another, and showed a nearly identical burst morphology from one spontaneous discharge to the next.

EXAMPLE 7

Effects of Low-Chloride Treatment on Spontaneous Synaptic Activity

It is possible that the anti-epileptic effects associated with chloride-cotransport antagonism are mediated by some action on transmitter release. Blockade of chloride-cotransport could alter the amount or timing of transmitter released from terminals, thus affecting neuronal synchronization. To test whether low-$[Cl^-]_o$ exposure affected mechanisms associated with transmitter release, intracellular CA1 responses were recorded simultaneously with CA1 and CA3 field responses during a treatment which dramatically increases spontaneous synaptic release of transmitter from presynaptic terminals.

Increased spontaneous release of transmitter was induced by treatment with 4-AP (100 µM). After 40 minutes exposure to 4-AP-containing medium, spontaneous synchronized burst discharges were recorded in area CA1 and CA3. Switching to 4-AP-containing low-$[Cl^-]_o$ medium led initially, as was shown previously, to enhanced spontaneous bursting. High-grain intracellular recordings showed that high-amplitude spontaneous synaptic activity was elicited by 4-AP treatment. Further exposure to low-chloride medium blocked spontaneous burst discharge in CA1, although CA3 continued to discharge spontaneously. At this time, CA1 intracellular recordings showed that spontaneous synaptic noise was further increased, and remained so for prolonged exposure times to 4-AP-containing low-chloride medium. These data suggest that mechanisms responsible for synaptic release from terminals are not adversely affected by low-chloride exposure in a manner that could explain the blockade of 4-AP-induced spontaneous bursting in CA1. These results also eliminate the possibility that the effects of low-$[Cl^-]_o$ exposure are due to alterations in CA1 dendritic properties which would compromise their efficiency in conducting PSPs to the soma.

Experimental Methods for Examples 8 to 12

In all of the following experiments, $[Cl^-]_o$ was reduced by equimolar replacement of NaCl with $Na^+$-gluconate. Gluconate was used rather than other anion replacements for several reasons. First, patch-clamp studies have demonstrated that gluconate appears to be virtually impermeant to chloride channels, whereas other anions (including methylsulfate, sulfate, isethionate, and acetate) are permeable to varying degrees. Second, transport of extracellular potassium through glial NKCC1 cotransport is blocked when extracellular chloride is replaced by gluconate but is not completely blocked when replaced by isethionate. Since this furosemide-sensitive cotransporter plays a significant role in cell swelling and volume changes of the extracellular space (ECS), we wished to use the appropriate anion replacement so that the effects of our treatment would be comparable to previous furosemide experiments (Hochman et al. *Science*, 270:99-102, 1995; U.S. Pat. No. 5,902,732). Third, formate, acetate, and propionate generate weak acids when employed as $Cl^-$ substitutes and lead to a prompt fall in intracellular pH; gluconate remains extracellular and has not been reported to induce intracellular pH shifts. Fourth, for purposes of comparison we wished to use the same anion replacement that had been used in previous studies examining the effects of low-$[Cl^-]_o$ on activity-evoked changes of the ECS.

There is some suggestion that certain anion-replacements might chelate calcium. Although subsequent work has failed to demonstrate any significant ability of anion-substitutes to chelate calcium, there is still some concern in the literature regarding this issue. Calcium chelation did not appear to be an issue in the following experiments, since resting membrane potentials remained normal and synaptic responses (indeed, hyperexcitable synaptic responses) could be elicited even after several hours of exposure to medium in which $[Cl^-]_o$ had been reduced by gluconate substitution. Further, we confirmed that calcium concentration in our low-$[Cl^-]_o$-medium was identical to that in our control-medium by measurements made with $Ca^{2+}$-selective microelectrodes.

Sprague-Dawley adult rats were prepared as previously described. Briefly, transverse hippocampal slices, 400 μm thick, were cut using a vibrating cutter. Slices typically contained the entire hippocampus and subiculum. After cutting, slices were stored in an oxygenated holding chamber for at least one hour prior to recording. All recordings were acquired in an interface type chamber with oxygenated (95% $O_2$/5% $CO_2$) artificial cerebral spinal fluid (ACSF) at 34°-35° C. Normal ACSF contained (in mmol/l): 124 NaCl, 3 KCl, 1.25 $NaH_2PO_4$, 1.2 $MgSO_4$, 26 $NaHCO_3$, 2 $CaCl_2$, and 10 dextrose. In some experiments, normal or low-chloride medium was used containing bicuculline (20 μM), 4-AP (100 μM), or high-$K^+$ (12 mM). Low-chloride solutions (7, 16, and 21 mM $[Cl^-]_o$) were prepared by equimolar replacement of NaCl with $Na^+$-gluconate (Sigma Chemical Co., St. Louis, Mo.). All solutions were prepared so that they had a pH of approximately 7.4 and an osmolarity of 290-300 mOsm at 35° C. and at equilibrium from carboxygenation with 95% $O_2$/5% $CO_2$.

Sharp-electrodes filled with 4 M potassium acetate were used for intracellular recordings from CA1 pyramidal cells. Field recordings from the CA1 or CA3 cell body layers were acquired with low-resistance glass electrodes filled with NaCl (2 M). For stimulation of the Schaffer collateral pathway, a small monopolar electrode was placed on the surface of the slice midway between areas CA1 and CA3. Spontaneous and stimulation-evoked activities from field and intracellular recordings were digitized (Neurocorder, Neurodata Instruments, New York, N.Y.), and stored on video tape. Axo-Scope software (Axon Instruments Inc.) on a PC-computer was used for off-line analyses of data.

Ion-selective microelectrodes were fabricated according to standard methods well known in the art. Double-barreled pipettes were pulled and broken to a tip diameter of approximately 3.0 μm. The reference barrel was filled with ACSF and the other barrel was sylanized and the tip back-filled with a resin selective for $K^+$ (Corning 477317). The remainder of the sylanized barrel was filled with KCl (140 mM). Each barrel was led, via Ag/AgCl wires, to a high impedance dual-differential amplifier (WPI FD223). Each ion-selective microelectrode was calibrated by the use of solutions of known ionic composition and was considered suitable if it was characterized by a near-Nernstian slope response and if it remained stable throughout the duration of the experiment.

After placement in the interface chamber, slices were superfused at approximately 1 ml/minute. At this flow-rate, it took approximately 8-10 minutes for changes in perfusion media to be completed. All of the times reported here have taken this time-delay into account and have an error of approximately ±2 minutes.

EXAMPLE 8

Effects of Low-$[Cl^-]_o$ on CA1 Field Recordings

Other studies have shown that prolonged exposure of cortical and hippocampal slices to low-$[Cl^-]_o$ does not affect basic intrinsic and synaptic properties such as input resistance, resting membrane potential, depolarization-induced action-potential generation, or excitatory synaptic transmission. A previous study has also partly characterized the epileptogenic properties of low-$[Cl^-]_o$ exposure to the CA1 area of hippocampus. The following studies were performed to observe the times of onset and possible cessation of low-$[Cl^-]_o$-induced hyperexcitability and hypersynchronization. Slices (n=6) were initially perfused with normal medium until stable intracellular and field recordings were established in a CA1 pyramidal cell and the CA1 cell body layer, respectively. In two experiments, the same cell was held throughout the entire length of the experiment (greater than 2 hours). In the remaining experiments (n=4), the initial intracellular recording was lost during the sequence of medium changes and additional recordings were acquired from different cells. Patterns of neuronal activity in these experiments were identical to those seen when a single cell was observed.

The field and intracellular electrodes were always placed in close proximity to one another (<200 μm). In each case, after approximately 15-20 minutes exposure to the low-$[Cl^-]_o$-medium (7 mM), spontaneous bursting developed, first at the cellular level, and then in the field. This spontaneous field activity, representing synchronized burst discharge in a large population of neurons, lasted from 5-10 minutes, after which time the field recording became silent. When the field first became silent, the cell continued to discharge spontaneously. This result suggests that population activity has been "desynchronized" while the ability of individual cells to discharge has not been impaired. After approximately 30 minutes exposure to low-$[Cl^-]_o$-medium, intracellular recording showed that cells continued to discharge spontaneously even though the field remained silent. The response of the cell to intracellular current injection at two time points demonstrated that the cell's ability to generate action potentials had not been impaired by low-$[Cl^-]_o$ exposure. Further, electrical stimulation in CA1 stratum radiatum elicited burst discharges, indicating that a hyperexcitable state was maintained in the tissue.

EXAMPLE 9

Effects of low-$[Cl-]_o$ on High-$[K+]_o$-Induced Epileptiform Activity in CA1

The previous set of experiments showed that tissue exposure to low-$[Cl^-]_o$ medium induced a brief period of spontaneous field potential bursting which ceased within 10 minutes. If a reduction of $[Cl^-]_o$ is indeed eventually capable of blocking spontaneous epileptiform (i.e. synchronized) bursting, then these results suggest that anti-epileptic effects would likely be observable only after this initial period of bursting activity has ceased. We therefore examined the temporal effects of low-$[Cl^-]_o$-treatment on high-$[K^+]_o$-induced bursting activity. Slices (n=12) were exposed to medium in which $[K^+]_o$ had been increased to 12 mM, and field potentials were recorded with a field electrode in the CA1 cell body layer. Spontaneous field potential bursting was observed for at least 20 minutes, and then the slices were exposed to medium in which $[K^+]_o$ was maintained at 12 mM, but $[Cl^-]_o$ was reduced to 21 mM. Within 15-20 minutes after the tissue was exposed to the low-$[Cl^-]_o$/high-$[K^+]_o$-medium, the burst amplitude increased and each field event had a longer duration. After a brief period of this facilitated field activity (lasting 5-10 minutes), the bursting stopped. To test whether this blockade was reversible, after at least 10 minutes of field potential silence, we switched back to high-$[K^+]_o$-medium with normal $[Cl^-]_o$. The bursting returned within 20-40 minutes. Throughout each experiment, the CA1 field response to Schaffer collateral stimulation was monitored. The largest field responses were recorded just before the cessation of spontaneous bursting, during the period when the spontaneous bursts had the largest amplitude. Even after the blockade of spontaneous bursting, however, multiple population spikes were elicited by Schaffer collateral stimulation, indicating that synaptic transmission was intact, and that the tissue remained hyperexcitable.

In four slices, intracellular recordings from CA1 pyramidal cells were acquired along with the CA1 field recording. During the period of high-$[K^+]_o$-induced spontaneous bursting, hyperpolarizing current was injected into the cell so that postsynaptic potentials (PSPs) could be better observed. After low-$[Cl^-]_o$-blockade of spontaneous bursting, spontaneously occurring action potentials and PSPs were still observed. These observations further support the view that synaptic activity, per se, was not blocked by the low-$[Cl^-]_o$ treatment.

EXAMPLE 10

Low-$[Cl^-]_o$-Blockade of Epileptiform Activity Induced by 4-AP, High-$[K^+]_o$, and Bicuculline in CA1 and CA3

We next tested whether low-$[Cl^-]_o$ treatment could block epileptiform activity in areas CA1 and CA3, which was elicited by different pharmacological treatments, as we had shown for furosemide treatment. For this set of experiments, we chose to test the effects of low-$[Cl^-]_o$ treatment on spontaneous bursting which had been induced by high-$[K^+]_o$ (12 mM) (n=5), 4-AP (100 µM) (n=4), and bicuculline (20 and 100 µM) (n=5). In each set of experiments, field responses were recorded simultaneously from areas CA1 and CA3, and in each case, the spontaneous epileptiform activity in both areas CA1 and CA3, was reversibly blocked within 30 minutes after $[Cl^-]_o$ in the perfusion medium had been reduced to 21 mM. These data suggest that, like furosemide, low-$[Cl^-]_o$ reversibly blocks spontaneous bursting in several of the most commonly studied in vitro models of epileptiform activity.

EXAMPLE 11

Comparison Between Low-$[Cl^-]_o$ and Furosemide on Blockade of High-$[K^+]_o$-Induced Epileptiform Activity The data from the previous sets of experiments are consistent with the hypothesis that the anti-epileptic effects of both low-$[Cl^-]_o$ and furosemide are mediated by their actions on the same physiological mechanisms. To further test this hypothesis, we compared the temporal sequence of effects of low-$[Cl^-]_o$ (n=12) and furosemide (2.5 and 5 mM) (n=4) on high-$[K^+]_o$-induced bursting, as recorded with a field electrode in CA1. We found that both low-$[Cl^-]_o$ and furosemide treatment induced a similar temporal sequence of effects: an initial brief period of increased amplitude of field activity, and then blockade (reversible) of spontaneous field activity. In both cases, electrical stimulation of the Schaffer collaterals elicited hyperexcited responses even after the spontaneous bursting had been blocked.

EXAMPLE 12

Consequences of Prolonged Exposure to Low-$[Cl-]_o$ Medium with Varied $[K+]_o$

In the preceding experiments, we monitored field activity in some slices for >1 hour after the spontaneous bursting had been blocked by low-$[Cl^-]_o$ exposure. After such prolonged low-$[Cl^-]_o$ exposure, spontaneous, long-lasting, depolarizing shifts developed. The morphology and frequency of these late-occurring field events appeared to be related to the extracellular potassium and chloride concentrations. Motivated by these observations, we performed a set of experiments in which we systematically varied $[Cl^-]_o$ and $[K^+]_o$ and observed the effects of these ion changes on the late-occurring spontaneous field events.

In our first set of experiments, slices were exposed to medium containing low-$[Cl^-]_o$ (7 mM) and normal-$[K^+]_o$ (3 mM) (n=6). After 50-70 minutes exposure to this medium, spontaneous events were recorded in area CA1; these events appeared as 5-10 mV negative shifts in the DC field, with the first episode lasting for 30-60 seconds. Each subsequent episode was longer than the previous one. This observation suggested that ion-homeostatic mechanisms were diminished over time as a result of the ion concentrations in the bathing medium. In some experiments (n=2) in which these negative DC field shifts had been induced, intracellular recordings from CA1 pyramidal cells were acquired simultaneously with the CA1 field recordings.

For these experiments, the intracellular and field recordings were acquired close to one another (<200 µm). Prior to each negative field shift (10-20 seconds), the neuron began to depolarize. Cellular depolarization was indicated by a decrease in resting membrane potential, an increase in spontaneous firing frequency, and a reduction of action potential amplitude. Coincident with the onset of the negative field shifts, the cells became sufficiently depolarized so that they were unable to fire spontaneous or current-elicited (not shown) action potentials. Since neuronal depolarization began 10-20 seconds prior to the field shift, it may be that a gradual increase in extracellular potassium resulted in the depolarization of a neuronal population, thus initiating these field events. Such an increase in $[K^+]_o$ might be due to alterations of the chloride-dependent glial cotransport mechanisms that normally move potassium from extracellular to intracellular spaces. To test whether increases in $[K^+]_o$ preceded these negative field shifts (and paralleled cellular depolarization), experiments (n=2) were performed in which a $K^+$-selective microelectrode was used to record changes in $[K^+]_o$.

In each experiment, the $K^+$-selective microelectrode and a field electrode were placed in the CA1 pyramidal layer close to one another (<200 µm), and a stimulation pulse was delivered to the Schaffer collaterals every 20 seconds so that the magnitude of the population spike could be monitored. Multiple spontaneously occurring negative field shifts were evoked by perfusion with low-$[Cl^-_o]$ (7 mM) medium. Each event was associated with a significant increase in $[K^+]_o$, with the $[K^+]_o$ increase starting several seconds prior to the onset of negative field shift. A slow 1.5-2.0 mM increase in $[K^+]_o$ occurred over a time interval of approximately 1-2 minute seconds prior to the onset of each event. The stimulation-evoked field responses slowly increased in amplitude over time, along with the increasing $[K^+]_o$, until just before the negative field shift.

In a second set of experiments (n=4), $[K^+]_o$ was increased to 12 mM and $[Cl-]_o$ was increased to 16 mM. After 50-90 minutes exposure to this medium, slow oscillations were recorded in area CA1. These oscillations were characterized by 5-10 mV negative DC shifts in the field potential and had a periodicity of approximately 1 cycle/40 seconds. Initially, these oscillations occurred intermittently and had an irregular morphology. Over time, these oscillations became continuous and developed a regular waveform. Upon exposure to furosemide (2.5 mM), the amplitude of the oscillations was gradually decreased and the frequency increased until the oscillations were completely blocked. Such low-$[Cl]_o$-induced oscillations in tissue slices have not been previously reported. However, the temporal characteristics of the oscillatory events bear a striking resemblance to the low-$[Cl]_o$-induced $[K^+]_o$ oscillations which were previously described in a purely axonal preparation.

In a third set of experiments (n=5) $[Cl^-]_o$ was further increased to 21 mM and $[K^+]_o$ was reduced back to 3 mM. In these experiments, single, infrequently occurring negative shifts of the field potential developed within 40-70 minutes (data not shown). These events (5-10 mV) lasting 40-60 seconds, occurred at random intervals, and maintained a relatively constant duration throughout the experiment. These events could sometimes be elicited by a single electrical stimulus delivered to the Schaffer collaterals.

Finally, in a final set of experiments (n=5), $[Cl^-]_o$ was kept at 21 mM and $[K^+]_o$ was raised to 12 mM. In these experiments, late-occurring spontaneous field events were not observed during the course of the experiments (2-3 hours).

EXAMPLE 13

Changes in $[K^+]_o$ During Low-Chloride Exposure

Sprague-Dawley adult rats were prepared as previously described. Transverse hippocampal slices, 400 µm thick, were cut with a vibrating cuter and stored in an oxygenated holding chamber for 1 hour before recording. A submersion-type chamber was used for $K^+$-selective microelectrode recordings. Slices were perfused with oxygenated (95% $O_2$/5% $CO_2$) artificial cerebrospinal fluid (ACSF) at 34-35° C. Normal ACSF contained 10 mM dextrose, 124 mM NaCl, 3 mM KCl, 1.25 mM $NaH_2PO_4$, 1.2 mM $MgSO_4$, 26 mM $NaHCO_3$ and 2 mM $CaCl_2$. In some experiments, normal or low-chloride medium was used containing 4-aminopyridine (4-AP) at 100 µM. Low-chloride solutions (21 mM $[Cl]_0$) were prepared by equimolar replacement of NaCl with $Na^+$-gluconate (Sigma Chemical Co.).

Field recordings from the CA1 or CA3 cell body layers were acquired with low-resistance glass electrodes filled with NaCl (2M). For stimulation of the Schaffer collateral pathway, a monopolar stainless-steel electrode was placed on the surface of the slide midway between areas CA1 and CA3. All recordings were digitized (Neurorocorder, Neurodata Instruments, New York, N.Y.) and stored on videotape.

$K^+$ selective microelectrodes were fabricated according to standard methods. Briefly, the reference barrel of a double-barreled pipette was filled with ACSF, and the other barrel was sylanized and the tip back-filled with KCl with $K^+$-selective resin (Corning 477317). Ion-selective microelectrodes were calibrated and considered suitable if they had a Nernstian slope response and remained stable throughout the duration of the experiment.

Exposure of hippocampal slices to low-$[Cl^-]_0$ medium has been shown to include a temporally-dependent sequence of changes on the activity of CA1 pyramidal cells, with three characteristics phases, as described above. In brief, exposure to low-$[Cl^-]_0$ medium results in a brief period of increased hyperexcitability and spontaneous epileptiform discharge. With further exposure to low-$[Cl^-]_0$ medium, spontaneous epileptiform activity is blocked, but cellular hyperexcitability remains, and action potential firing times become less synchronized with one another. Lastly, with prolonged exposure, the action potential firing times become sufficiently desynchronized so that stimulation-evoked field responses completely disappear, yet individual cells continue to show monosynapticlly-evoked responses to Schaffer collateral stimulation. The following results demonstrate that the antiepileptic effects of furosemide on chloride-cotransport antagonism are independent of direct actions on excitatory synaptic transmission, and are a consequence of a desynchronization of population activity with our any associated decrease in excitability.

In six hippocampal slices, $K^+$-selective and field microelectrodes were placed in the CA1 cell body layer, and a stimulating electrode was placed on the Schaffer collateral pathway, and single-pulse stimuli (300 µs) were delivered every 20 seconds. After stable baseline $[K^+]$ was observed for at least 20 minutes, the perfusion was switched to low-$[Cl^-]_0$ medium. Within 1-2 minutes of exposure to low-$[Cl^-]_0$ medium, the field responses became hyperexcitable as the $[K^+]_0$ began to rise. After approximately 4-5 minutes of exposure to low-$[Cl^-]_0$ medium, the magnitude of the field response diminished until it was completely abolished. The corresponding recording of $[K^+]_0$ showed that potassium began to rise immediately after exposure to low-$[Cl^-]_0$ medium, and that the peak of this $[K^+]_0$ rise corresponded in time to the maximally hyperexcitable CA1 field response. Coincident with the reduction of the magnitude of the field response, the $[K^+]_0$ began to diminish until after 8-10 minutes exposure to low-$[Cl^-]_0$ medium, it became constant for the remainder of the experiment at 1.8-2.5 mM above control levels. Four slices were switched back to control medium and allowed to fully recover. The experiment was then repeated with the $K^+$-selective microelectrode placed in the stratum radiatum. A similar sequence of changes in $[K^+]_0$ was observed in the dendritic layer, with the values of $[K^+]_0$ being 0.2-0.3 mM less than those observed in the cell body layers.

In four hippocampal slices, the responses of stimulation-evoked changes in $[K^+]_0$ between control conditions and after the CA1 field response was completely abolished by low-$[Cl^-]_0$ exposure were compared. In each slice, the $[K^+]_o$-selective measurements were acquired first in the cell body layer, and then after allowance for complete recovery in control medium, the experiment was repeated with the $K^+$-selective electrode moved to the stratum radiatum. Each stimulation trial consisted of a 10 Hz volley delivered to the Schaffer collateral for 5 seconds. The peak rises in $[K^+]_0$ were similar between control conditions an after prolonged exposure to low-$[Cl^-]_0$ medium, and between the cell body and dendritic layers. However, the recovery times observed after prolonged exposure to low-$[Cl^-]_0$ were significantly longer than those observed during control conditions.

These results demonstrate that the administration of furosemide resulted in increased $[K^+]_0$ in the extracellular spaces. Exposure of the brain tissue to low-$[Cl^-]_0$ medium immediately induced a rise in $[K^+]_0$ by 1-2 mM, which remained throughout the duration of exposure, and was coincident with the initial increase in excitability and the eventual abolishment of the CA1 field response. This loss of CA1 field response during low-$[Cl^-]_0$ exposure is most likely due to the desynchronization of neuronal firing times. Significantly, the stimulation-evoked increases in $[K^+]_0$, in both the cell body and dendritic layers were nearly identical before and after the complete low-$[Cl^-]_0$ blockade of the CA1 field response. This data suggests that comparable stimulation-evoked synaptic drive and action potential generation occurred under control conditions and after low $[Cl^-]_0$ blockade of the field. Together these data demonstrate that the antiepileptic and desynchronizing effects of the chloride-cotransport antagonist, furosemide, are independent of direct actions on excitatory synaptic transmission and are a consequence of a desynchronization of population activity without decrease in excitability.

EXAMPLE 14

Changes in Extracellular pH During Low-Chloride Exposure

Antagonists of the anion/chloride-dependent cotransporter, such as furosemide and low-$[Cl^-]_0$, may affect extracellular pH transients that might contribute to the maintenance of synchronized population activity. Rat hippocampal brain slices were prepared as described in Example 13, except the $NaHCO_3$ was substituted by equimolar amount of HEPES (26 nM) and an interface-type chamber was used.

In four hippocampal brain slices continuous spontaneous bursting was elicited by exposure to medium containing 100 μM 4-AP, as described in Example 13. Field recordings were acquired simultaneously from the cell body layers in areas CA1 and CA3. A stimulus delivered every 30 seconds to the Schaffer collaterals throughout the duration of the experiments. After at least 20 minutes of continuous bursting was observed, the slices were exposed to nominally bicarbonate free, 4-AP-containing HEPES medium. There were no significant changes observed in the spontaneous or stimulation-evoked field responses resulting from prolonged exposure (0.2 hours) to HEPES medium. After the slices had been exposed for at least 2 hours to the HEPES medium, the perfusion was switched to 4-AP-containing HEPES medium in which the $[Cl^-]_0$ had been reduced to 21 mM. Exposure to the low-$[Cl^-]_0$ HEPES medium induced the identical sequences of events, and at the same time course, as had previously been observed with low-$[Cl^-]_0$ $NaHCO_3$-containing medium. After complete blockade of spontaneous bursting, the perfusion medium was switched back to HEPES medium with normal $[Cl^-]_0$. Within 20-40 minutes, spontaneous bursting resumed. At the time the spontaneous bursting had resumed, the slices had been perfused with nominally bicarbonate-free HEPES medium for greater than 3 hours.

This data suggests that the actions of chloride-cotransport antagonism on synchronization and excitability are independent of affects on the dynamics of extracellular pH.

Figure 4A:
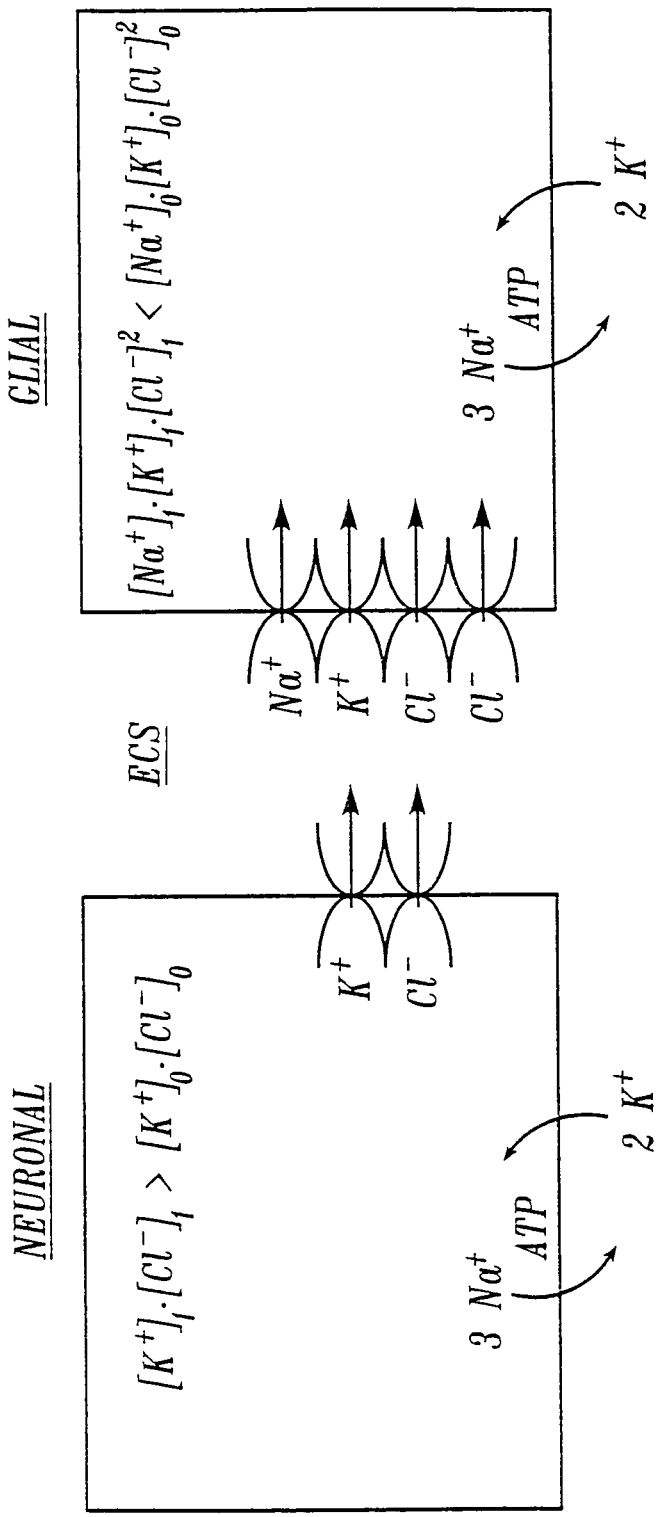
FIGS. 4A and 4B show a schematic diagram of ion co-transport under conditions of reduced chloride concentration.

FIG. 4 illustrates a schematic model of ion cotransport under conditions of reduced $[Cl^-]$. FIG. 4A, left panel, shows that the chloride gradient necessary for the generation of IPSPs in neurons is maintained by efflux of ions through a furosemide-sensitive $K^+$, $Cl^-$ cotransporter. Under normal conditions, a high concentration of intracellular potassium (maintained by the $3Na^+$, $2K^+$-ATPase pump) serves as the driving force for the extrusion of $Cl^-$ against its concentration gradient. In glial cells, as shown in the right panel of FIG. 4A, the movement of ions through the furosemide-sensitive NKCC co-transporter is from extracellular to intracellular spaces. The ion-gradients necessary for this cotransport are maintained, in part, by the "transmembrane sodium cycle": sodium ions taken into glial cells through NKCC cotransport are continuously extruded by the $3Na^+$, $2K^+$, -ATPase pump so that a low intracellular sodium concentration is maintained. The rate and direction of ion-flux through the furosemide-dependent cotransporters are functionally proportional to their ion-product differences written as $[K^+]_i \times [Cl^-]_i - [K^+]_o \times [Cl^-]_o$ for neuronal $K^+$, $Cl^-$ cotransport and as $[Na^+]_i \times [K^+]_i \times [Cl^-]_i^2 - [Na^+]_o \times [K^+]_o \times [Cl^-]_o^2$ for glial NKCC cotransport. The sign of these ion-product differences show the direction of ion transport with positive being from intracellular to extracellular spaces.

Figure 4B:
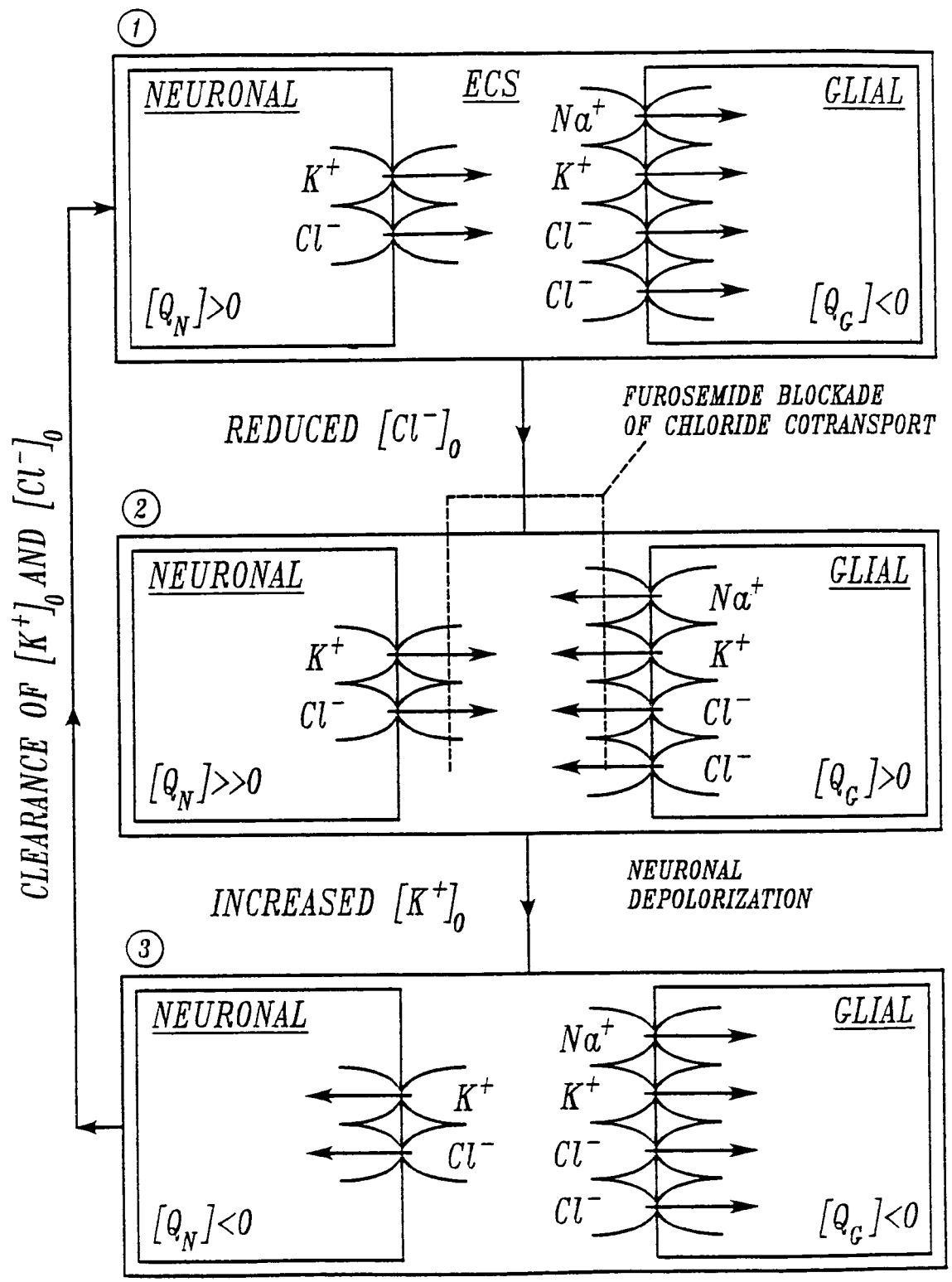

FIG. 4B shows a schematic phenomenological model that explains the emergence of the late-occurring spontaneous field events that arise as a result of prolonged low-$[Cl^-]_o$ exposure. We denote the ion-product differences for neurons and glia as QN and QG, respectively. Under control conditions (1), the differences of the ion-products for neurons are such that $K^+$ and $Cl^-$ are cotransported from intracellular to extracellular spaces (QN>0); the differences in ion-products for glial cells are such that $Na^+$, $K^+$ and $Cl^-$ are cotransported from the ECS to intracellular compartments (QG<0). When $[Cl^-]_o$ is reduced (2), the ion-product differences are altered so that neuronal efflux of KCl is increased; however, the glial icon cotransport is reversed (QG>0), so that there is a net efflux of KCl and NaCl from intracellular to extracellular spaces. These changes result in buildup of extracellular potassium over time. Eventually, $[K^+]_o$ reaches a level that induces the depolarization of neuronal populations, resulting in an even larger accumulation of $[K^+]_o$. This large accumulation of extracellular ions then serves to reverse the ion-product differences so that KCl is moved from extracellular to intracellular spaces (QN<0, QG<0) (3). Further clearance of the extracellular potassium eventually resets the transmembrane ion gradients to initial conditions. By cycling through this process, repetitive negative field events are generated.

EXAMPLE 15

Therapeutic Efficacy of Furosemide in the Alleviation of Pain Symptoms in an Animal Model of Neuropathic Pain The ability of furosemide to alleviate pain will be examined in rodents using the Chung model of neuropathic pain (see, for example, Walker et al. *Mol. Med. Today* 5:319-321, 1999). Sixteen adult male Long-Evans rats will be used in this study. All rats will receive spinal ligation of the L5 nerve as detailed below. Eight of the sixteen rats will receive an injection (intravenous) of furosemide and the remaining eight will receive intravenous injection of vehicle only. Pain threshold will be assessed immediately using the mechanical paw withdrawal test. Differences in pain thresholds between the two groups will be compared. If furosemide alleviates pain, the group with the furosemide treatment will exhibit a higher pain threshold than the group that received vehicle.

Chung Model of Neuropathy

Spinal nerve ligation is performed under isoflourane anesthesia with animals placed in the prone position to access the left L4-L6 spinal nerves. Under magnification, approximately one-third of the transverse process is removed. The L5 spinal nerve is identified and carefully dissected free from the adjacent L4 spinal nerve and then tightly ligated using a 6-0 silk suture. The wound is treated with an antiseptic solution, the muscle layer is sutured, and the incision is closed with wound clips. Behavioral testing of mechanical paw withdrawal threshold takes place within a 3-7 day period following the incision. Briefly, animals are placed within a Plexiglas chamber (20×10.5×40.5 cm) and allowed to habituate for 15 min. The chamber is positioned on top of a mesh screen so that mechanical stimuli can be administered to the plantar surface of both hindpaws. Mechanical threshold measurements for each hindpaw are obtained using an up/down method with eight von Frey monofilaments (5, 7, 13, 26, 43, 64, 106, and 202 mN). Each trial begins with a von Frey force of 13 mN delivered to the right hindpaw for approximately 1 sec, and then the left hindpaw. If there is no withdrawal response, the next higher force is delivered. If there is a response, the next lower force is delivered. This procedure is performed until no response is made at the highest force (202 mN) or until four stimuli are administered following the initial response. The 50% paw withdrawal threshold for each paw is calculated using the following formula: [Xth] log= [vFr] log+ky where [vFr] is the force of the last von Frey used, k=0.2268 which is the average interval (in log units) between the von Frey monofilaments, and y is a value that depends upon the pattern of withdrawal responses. If an animal does not respond to the highest von Frey hair (202 mN), then y=1.00 and the 50% mechanical paw withdrawal response for that paw is calculated to be 340.5 mN. Mechanical paw withdrawal threshold testing is performed three times and the 50% withdrawal values are averaged over the three trials to determine the mean mechanical paw withdrawal threshold for the right and left paw for each animal.

While the present invention has been described with reference to the specific embodiments thereof, it will be understood by those skilled in the art that various changes may be made and equivalents may be substituted without departing from the true spirit and scope of the invention. In addition, many modifications may be made to adapt a particular situation, material, composition of matter, method, method step or steps, for use in practicing the present invention. All such modifications are intended to be within the scope of the claims appended hereto.

All patents and publications cited herein and PCT Application WO 00/37616, published Jun. 29, 2000, are specifically incorporated by reference herein in their entireties.

SEQ ID NO: 1-2 are set out in the attached Sequence Listing. The codes for polynucleotide and polypeptide sequences used in the attached Sequence Listing conform to WIPO Standard ST.25 (1988), Appendix 2.

I claim:

1. A method for treating pain or the perception of pain in a mammalian subject in need thereof comprising administering an effective amount of a composition comprising a $Na^+K^+2Cl^-$ co-transporter antagonist to the subject.

2. The method of claim 1, wherein the $Na^+K^+2Cl^-$ co-transporter antagonist is a NKCC1 co-transporter antagonist.

3. The method of claim 1, wherein the antagonist is a loop diuretic.

4. The method of claim 3, wherein the antagonist is selected from the group consisting of: furosemide; bumetanide; ethacrynic acid; torsemide; azosemide; muzolimine; piretanide; and tripamide.

5. The method of claim 1, wherein the antagonist is selected from the group consisting of thiazide and thiazide-like diuretics.

6. The method of claim 5, wherein the antagonist is selected from the group consisting of bendroflumethiazide; benzthiazide; chlorothiazide; hydrochlorothiazide; hydroflumethiazide; methylclothiazide; polythiazide; trichlormethiazide; chlorthalidone; indapamide; metolazone; and quinethazone.

7. The method of claim 1, wherein the antagonist modulates extracellular ion composition and chloride gradients in nervous system tissue.

8. The method of claim 1, wherein the composition is administered orally, sublingually, nasally, transdermally, intravenously, intracranially, intraperitoneally, subcutaneously, intramuscularly, or by inhalation, spinal tap, direct intrathecal injection, administration into the cerebral spinal fluid via the spinal cord by injection or osmotic pump, or administration in a sustained release formulation.

9. The method of claim 1, wherein the pain is neuropathic pain and said neuropathic pain is selected from the group consisting of diabetic neuropathy; postherpetic neuralgia; cancer-related pain; neurotoxicity-induced pain; spinal cord injury; causalgia or reflex sympathetic dystrophy; trigeminal neuralgia; chronic lower back pain; and central post-stroke pain.

10. The method of claim 1, wherein the subject is a human.

11. The method of claim 1, wherein the pain is neuropathic pain and said neuropathic pain has the following etiologies: alcohol abuse; diabetes; eosinophilia-myalgia syndrome; Guillain-Barre syndrome; exposure to arsenic, lead, mercury, and thallium; HIV/AIDS; malignant tumors; amiodarone, aurothioglucose, cisplatinum, dapsone, stavudine, zalcitabine, didanosine, disulfiram, FK506, hydralazine, isoniazid, metronidazole, nitrofurantoin, paclitaxel, phenyloin and vincristine; monoclonal gammopathies; multiple sclerosis; post-stroke central pain, postherpetic neuralgia; carpal tunnel syndrome, cervical or lumbar radiculopathy, complex regional pain syndrome, spinal cord injury and stump pain; trigeminal neuralgia; vasculitis; vitamin B6 megadosing; and vitamin B12, B1, B6, or E deficiencies.

12. The method of claim 1, wherein the composition further comprises a component selected from the group consisting of: phenytoin; carbamazepine; barbiturates; Phenobarbital; pentobarbital: mephobarbital: trimethadione: mephenytoin; paramethadione; phenthenylate; phenacemide; metharbital; benzchlorpropanmide; phensuximide; primidone; methsuximide; ethotoin; aminoglutehimide; diazepam; clonazepam; clorazepate; fosphenytoin; ethosuximide; valporate; felbamate; gabapentin; lamotrigine; topiramate; vigrabatrin; tiagabine; zonisamide; clobazam; thiopental; midazoplam; propofol; levetiracetam; oxcarbazepine; CCPene; GYK152466; sumatriptan; non-steroidal anti-inflammatory drugs; neuroleptics; corticosteroids; vasoconstrictors; beta-blockers; antidepressants; anticonvulsants; Depakote; Ergot alkaloids; tryptans; Acetaminophen; caffeine; Ibuprofen; Proproxyphene; oxycodone; codeine; isometheptene; serotonin receptor agonists; ergotamine; dihydroergotamine; sumatriptan; propranolol; metoprolol; atenolol; timolol; nadolol; nifeddipine; nimodipine; verapamil; aspirin; ketoprofen; tofenamic acid; mefenamic acid; naproxen; methysergide; paracetamol; clonidine; lisuride; iprazochrome; butalbital; benzodiazepines; divalproex sodium, a blood brain barrier permeability enhancer and a hyperosmotic agent.

13. The method of claim 12, wherein said administering comprises simultaneous or sequential administration of one or more agents in the same formulation or unit dosage form or in separate formulations or unit dosage forms.

* * * * *